United States Patent
Caruso et al.

(10) Patent No.: US 8,426,417 B2
(45) Date of Patent: *Apr. 23, 2013

(54) SUBSTITUTED PYRROLO-PYRIMIDINE DERIVATIVES, PROCESS FOR THEIR PREPARATION AND THEIR USE AS KINASE INHIBITORS

(75) Inventors: Michele Caruso, Milan (IT); Italo Beria, Nerviano (IT); Maria Gabriella Brasca, Cusago (IT); Helena Posteri, Travedona Monate (IT); Marina Caldarelli, Milan (IT); Walter Ceccarelli, Corsico (IT); Barbara Valsasina, Milan (IT)

(73) Assignee: Nerviano Medical Sciences S.r.l., Nerviano (MI) (IT)

(*) Notice: Subject to any disclaimer, the term of this patent is extended or adjusted under 35 U.S.C. 154(b) by 303 days.

This patent is subject to a terminal disclaimer.

(21) Appl. No.: 12/679,716

(22) PCT Filed: Sep. 25, 2008

(86) PCT No.: PCT/EP2008/062853
§ 371 (c)(1),
(2), (4) Date: Mar. 24, 2010

(87) PCT Pub. No.: WO2009/040399
PCT Pub. Date: Apr. 2, 2009

(65) Prior Publication Data
US 2012/0122882 A1 May 17, 2012

(30) Foreign Application Priority Data
Sep. 28, 2007 (EP) .................. 07117529

(51) Int. Cl.
C07D 403/04 (2006.01)
C07D 471/04 (2006.01)
A61K 31/506 (2006.01)

(52) U.S. Cl.
USPC ............... 514/252.18; 514/252.19; 514/275; 544/295; 544/331

(58) Field of Classification Search .......... 544/295, 544/331; 514/252.18, 252.19, 275
See application file for complete search history.

(56) References Cited

FOREIGN PATENT DOCUMENTS

| EP | 1 598 343 A1 | 11/2005 |
|---|---|---|
| WO | WO 02/079193 A1 | 10/2002 |
| WO | WO 2004/043953 A1 | 5/2004 |
| WO | WO 2005/014572 A1 | 2/2005 |
| WO | WO 2006/071644 A1 | 7/2006 |
| WO | WO 2007/042786 A2 | 4/2007 |
| WO | WO 2007/110344 A1 | 10/2007 |

OTHER PUBLICATIONS

Layzer, Degenerative Diseases of the Nervous System, Cecil Textbook of Medicine, 20th Edition, vol. 2, pp. 2050-2057 (1996).*
Damasio, Alzheimer's Disease and Related Dementias, Cecil Textbook of Medicine, 20th Edition, vol. 2, pp. 1992-1996 (1996).*
Simone, Oncology: Introduction, Cecil Textbook of Medicine, 20th Edition, vol. 1, pp. 1004-1010, 1996.*
Douglas, Jr., Introduction to Viral Diseases, Cecil Textbook of Medicine, 20$^{th}$ Edition, vol. 2, pp. 1739-1747, 1996.*
Bosseray et al., PubMed Abstract (Pathol Biol (Paris) 50(8):483-92), 2002.*
Goff, PubMed Abstract (J Gene Med. 3(6):517-28), 2001.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Razonable et al., PubMed Abstract (Herpes 10(3):60-5), 2003.*
International Search Report dated Feb. 5, 2009 received from the European Patent Office.

* cited by examiner

*Primary Examiner* — Deepak Rao
(74) *Attorney, Agent, or Firm* — Scully, Scott, Murphy & Presser, P.C.

(57) ABSTRACT

Substituted pyrrolo-pyrimidine derivatives of formula (I) and pharmaceutically acceptable salts thereof, as defined in the specification, process for their preparation and pharmaceutical compositions comprising them are disclosed; the compounds of the invention may be useful in therapy in the treatment of diseases associated with a dysregulated protein kinase activity, like cancer.

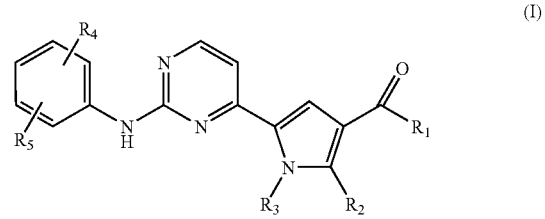

15 Claims, No Drawings

SUBSTITUTED PYRROLO-PYRIMIDINE DERIVATIVES, PROCESS FOR THEIR PREPARATION AND THEIR USE AS KINASE INHIBITORS

The present invention relates to certain substituted pyrrolo-pyrimidine compounds, which modulate the activity of protein kinases. The compounds of this invention are therefore useful in treating diseases caused by dysregulated protein kinase activity. The present invention also provides methods for preparing these compounds, pharmaceutical compositions comprising these compounds, and methods of treating diseases utilizing pharmaceutical compositions comprising these compounds.

The use of mitotic inhibitors in cancer therapy is a widely accepted clinical strategy for the treatment of a broad range of human cancers. Taxanes (Paclitaxel and Docetaxel) and Vinca Alkaloids (Vincristine and Vinblastine) work by either stabilizing or destabilizing microtubules with catastrophic consequences in cells progressing through mitosis. They are first line therapeutics for several tumour types and second line in cisplatin-refractory ovarian, breast, lung, bladder and esophagus cancers (Taxanes). However, due to the role of microtubules in processes such as cell movement, phagocytosis and axonal transport certain toxicities such as peripheral neuropathy are frequently observed with these agents. Progression through mitosis is a requirement of all proliferating cells and hence cancer therapies that have targets in mitosis are generally applicable to a wide range of tumour types. Several protein kinases play key roles in the orchestration of the cell cycle and some of them are already subject to targeted therapies in the oncology setting including Cdk-2 and Aurora-A. The fidelity of mitosis is of paramount importance and several "checkpoints" exist in normal cells to maintain chromosome integrity during the cell cycle. These checkpoints often go away during oncogenic transformation and this permits cancer cells to tolerate anueploidy and chromosomal instability Inhibition of mitosis in "checkpoint compromised" tumour cells should have catastrophic consequences as cancer cells try to carry forward an aberrant mitosis.

The Polo-like kinase family, comprising 4 serine/threonine kinases (Plk-1-4), are predominantly involved in the entry into, progression through and exit from mitosis. These kinases are characterized by having an n-terminal kinase domain and a unique, c-terminal, "Polo-Box" domain. This domain is responsible for targeting the kinase to various mitotic structures (centrosomes, kinetochores, spindle poles, midbody) and the temporal and spatial regulation of Plks are important for normal progression through mitosis (reviewed in van Vugt and Medema, Oncogene 2005, 24(17):2844-59; Barr et al, Nat Rev Mol Cell Biol. 2004, 5(6):429-40; Dai and Cogswell, Prog Cell Cycle Res. 2003, 5:327-34; Glover et al, Genes Dev. 1998, 12(24):3777-87).

The most characterized member of the family is Plk-1 and its activity has been implicated in several processes during mitosis including the G2/M transition by regulating Cdk-1 activity in multiple ways (activation of Cdc25c, nuclear translocation of cyclin B, inactivation of Myt-1 and Wee-1) (Inoue et al, EMBO J. 2005, 24(5):1057-67; van Vugt et al, J Biol Chem. 2004, 9(35):36841-54; Watanabe et al, Proc Natl Acad Sci USA. 2004, 101(13):4419-24; Nakajima et al, J Biol Chem. 2003, 278(28):25277-80; Toyoshima-Morimoto et al, J Biol Chem. 2002, 277(50):48884-8; Bartholomew et al, Mol Cell Biol., 2001 21(15):4949-59; Qian et al, Mol Biol Cell. 2001, 12(6):1791-9; Roshak et al, Cell Signal. 2000, 12(6):405-11); centrosome maturation and separation; regulation of chromosomal-arm cohesion at prophase and sister chromatid separation at metaphase/anaphase transition; activation of the Anaphase Promoting Complex to start mitotic exit; cytokinesis. Plk-1 is over-expressed in several tumour cells including breast, ovarian, non small cell lung, colon, head and neck, endometrial and esophageal carcinomas and its over-expression often correlates with poor prognosis. Disruption of Plk-1 function by various means in tumoural cells (siRNA and antisense ablation, dominant negative proteins and immunodepletion) results in an aberrant mitosis followed by mitotic catastrophy whilst causing a "checkpoint-mediated" cell cycle arrest in normal cells. Thus, pharmacological attenuation of Plk-1 function may have a therapeutic benefit in the treatment of several diverse cancers.

SUMMARY OF THE INVENTION

Several pyrrolo-pyrimidine derivatives for the treatment of hyperproliferative diseases such as cancer have been disclosed in WO 2006/071644 (Vertex Pharm Inc.), WO 2005/014572, WO 2007/068728 and WO 2007/071621 (Pfizer Italia Srl). The application WO2007/110344 in the name of the same Applicant, also describes and claims pyrrolo-pyrimidine derivatives, but none of the compounds exemplified therein are encompassed in the general formula (I) of the present application.

A specific compound claimed in the aforementioned WO 2005/014572 is excluded from the present general formula.

Despite these developments, there is still need for effective agents for said diseases.

The present inventors have now discovered that compounds of formula (I), described below, are kinase inhibitors and are thus useful in therapy as antitumor agents and lack, in terms of both toxicity and side effects, the aforementioned drawbacks associated with currently available antitumor drugs.

Accordingly, a first object of the present invention is to provide a substituted pyrrolo-pyrimidine compound represented by formula (I),

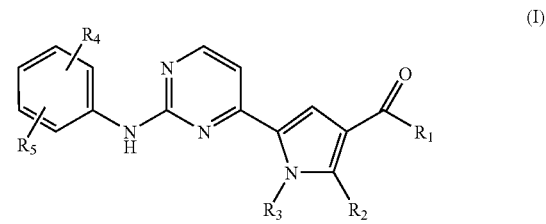

wherein:
$R_1$ is —OR' or —NR'R", wherein R' and R" are, each independently, hydrogen or an optionally substituted group selected from straight or branched $C_1$-$C_6$ alkyl, $C_2$-$C_6$ alkenyl, $C_2$-$C_6$ alkynyl, $C_3$-$C_6$ cycloalkyl and heterocyclyl;
$R_2$ is hydrogen, or
$R_1$ and $R_2$ taken together are a —NH—$CH_2$—$CH_2$— chain and form a 6-membered lactam fused with the pyrrole ring;
$R_3$ is hydrogen or an optionally substituted group selected from straight or branched $C_1$-$C_6$ alkyl, $C_2$-$C_6$ alkenyl, $C_2$-$C_6$ alkynyl, $C_3$-$C_6$ cycloalkyl and heterocyclyl;
$R_4$ and $R_5$ are, each independently, hydrogen, halogen, nitro, cyano, a group —O—$R_3$, —O—CO—$R_3$, —CO—O—$R_3$, —N—$(R_3)_2$, —N($R_3$)—CO—$R_3$, —CO—N$(R_3)_2$, —N($R_3$)CON$(R_3)_2$, —CO—$R_3$, —S—$R_3$, —S(O)$_2$—$R_3$, or an optionally substituted group selected from straight or branched $C_1$-$C_6$ alkyl, polyfluorinated alkyl, polyfluorinated alkoxy, $C_3$-$C_6$ cycloalkyl, $C_2$-$C_6$ alkenyl, $C_2$-$C_6$ alkynyl, heterocyclyl, heterocyclylalkyl, aryl, arylalkyl, heteroaryl, heteroarylalkyl and hydroxyalkyl, wherein $R_3$ is as defined above;
and pharmaceutically acceptable salts thereof, with the proviso that the following compound is excluded:
2-(2-phenylamino-pyrimidin-4-yl)-1,5,6,7-tetrahydro-pyrrolo[3,2-c]pyridin-4-one.

The present invention also provides methods of preparing the substituted pyrrolo-pyrimidine compounds, represented by formula (I), prepared through a process consisting of standard synthetic transformations.

The present invention also provides a method for treating diseases caused by and/or associated with dysregulated protein kinase activity, particularly PLK family, protein kinase C in different isoforms, Met, PAK-4, PAK-5, ZC-1, STLK-2, DDR-2, Aurora 1, Aurora 2, Bub-1, Chk1, Chk2, HER2, raf1, MEK1, MAPK, EGF-R, PDGF-R, FGF-R, IGF-R, PI3K, wee1 kinase, Src, Ab1, Akt, MAPK, ILK, MK-2, IKK-2, Cdc7, Nek, Cdk/cyclin kinase family, more particularly PLK-1 and PLK-3, which comprises administering to a mammal, in need thereof, an effective amount of a substituted pyrrolo-pyrimidine compound represented by formula (I) as defined above.

A preferred method of the present invention is to treat a disease caused by and/or associated with dysregulated protein kinase activity selected from the group consisting of cancer, cell proliferative disorders, viral infections, autoimmune and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, in particular the prevention of AIDS development in HIV-infected individuals.

In addition, the method of the present invention also provides tumor angiogenesis and metastasis inhibition as well as the treatment of organ transplant rejection and host versus graft disease.

In a further preferred method the present invention further comprises subjecting the mammal in need thereof to a radiation therapy or chemotherapy regimen in combination with at least one cytostatic or cytotoxic agent.

Moreover the invention provides a method for inhibiting PLK-1 and PLK-3 protein activity which comprises contacting the said protein with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention further provides a pharmaceutical composition comprising a compound of formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides the use of a compound of formula (I) or a pharmaceutically acceptable salt thereof, as defined above, in the manufacture of a medicament with antitumor activity.

Finally, the invention provides a compound of formula (I) or a pharmaceutically acceptable salt thereof, as defined above, for use in a method of treating cancer.

DETAILED DESCRIPTION OF THE INVENTION

Unless otherwise specified, when referring to the compounds of formula (I) per se as well as to any pharmaceutical composition thereof or to any therapeutic treatment comprising them, the present invention includes all of the isomers, tautomers, hydrates, solvates, complexes, metabolites, prodrugs, carriers, N-oxides and pharmaceutically acceptable salts of the compounds of this invention. Unless otherwise specified, when referring to the compounds of formula (I) per se as well as to any pharmaceutical composition thereof or to any therapeutic method of treatment comprising them, the present invention includes all the hydrates, solvates, complexes, metabolites, prodrugs, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

Prodrugs are any covalently bonded compounds, which release in vivo the active parent drug according to formula (I).

N-oxides are compounds of formula (I) wherein nitrogen and oxygen are tethered through a dative bond.

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases wherein compounds may exist in tautomeric forms, such as keto-enol tautomers, each tautomeric form is contemplated as being included within this invention whether existing in equilibrium or predominantly in one form.

Compounds of formula (I) wherein $R_1$ and $R_2$ taken together "are a —NH—$CH_2$—$CH_2$— chain and form a 6-membered lactam fused with the pyrrole ring", are represented by the general formula (Ia),

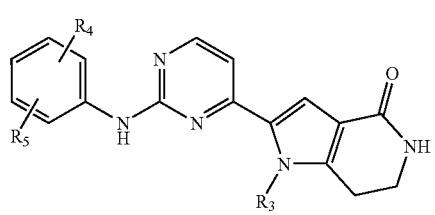

(Ia)

wherein $R_3$, $R_4$ and $R_5$ are as defined above.

Compounds of formula (I) wherein $R_1$ is —OR' and R' is as defined above except hydrogen, are represented by the general formula (Ib),

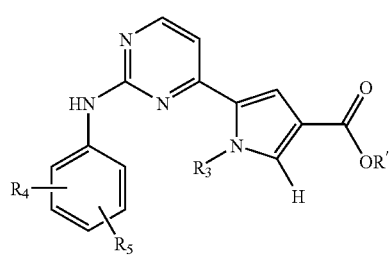

(Ib)

wherein $R_3$, $R_4$ and $R_5$ are as defined above.

With the term "straight or branched $C_1$-$C_6$ alkyl", hence comprehensive of $C_1$-$C_4$ alkyl, we intend any of the groups such as, for instance, methyl, ethyl, n-propyl, isopropyl, n-butyl, isobutyl, tert-butyl, sec-butyl, n-pentyl, n-hexyl, and the like.

With the term "$C_3$-$C_6$ cycloalkyl" we intend, unless otherwise provided, 3- to 6-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 7-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "$C_2$-$C_6$ alkenyl" we intend an aliphatic $C_2$-$C_6$ hydrocarbon chain containing at least one carbon-carbon double bond and which can be straight or branched. Representative examples include, but are not limited to, ethenyl, 1-propenyl, 2-propenyl, 1- or 2-butenyl, and the like.

With the term "$C_2$-$C_6$ alkynyl" we intend an aliphatic $C_2$-$C_6$ hydrocarbon chain containing at least one carbon-carbon triple bond and which can be straight or branched. Representative examples include, but are not limited to, ethynyl, 1-propynyl, 2-propynyl, 1- or 2-butynyl, and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non limiting examples of such aryl groups are phenyl, α- or β-naphthyl or biphenyl groups.

The term "heteroaryl" refers to aromatic heterocyclic rings, typically 5- to 7-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the present invention and unless otherwise provided, any of the above $R_3$, $R_4$, $R_5$, R', and R" group may be optionally substituted, in any of their free positions, by one or more groups, for instance 1 to 6 groups, independently selected from: halogen, nitro, oxo groups (═O), cyano, $C_1$-$C_6$ alkyl, polyfluorinated alkyl, polyfluorinated alkoxy, $C_2$-$C_6$ alkenyl, $C_2$-$C_6$ alkynyl, hydroxyalkyl, aryl, arylalkyl, heteroaryl, heteroarylalkyl, heterocyclyl, heterocyclylalkyl, $C_3$-$C_6$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonylamino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyamino carbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn, whenever appropriate, each of the above substituent may be further substituted by one or more of the aforementioned groups.

With the term halogen atom we intend a fluorine, chlorine, bromine or iodine atom.

With the term cyano we intend a —CN residue.

With the term nitro we intend a —NO$_2$ group.

With the term polyfluorinated alkyl or polyfluorinated alkoxy we intend any of the above straight or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term hydroxyalkyl we intend any of the above $C_1$-$C_6$ alkyl, bearing an hydroxyl group such as, for instance, hydroxymethyl, 2-hydroxyethyl, 3-hydroxypropyl and the like.

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_6$ cycloalkyl and heterocyclyl moieties are as above defined. Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, lactic, oxalic, fumaric, malonic, malic, maleic, tartaric, citric, benzoic, cinnamic, mandelic, methanesulphonic, isethionic and salicylic acid. Preferably, the acid addition salt of the compounds of the invention is selected between the hydrochloride or mesylate salt.

Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

A preferred class of compounds of formula (I) are the compounds wherein:
$R_1$ is —OH or —NR'R" wherein R' and R" are as defined above.

Another preferred class of compounds of formula (I) are the compounds wherein the position of the substituents $R_4$ and $R_5$ are as reported below:

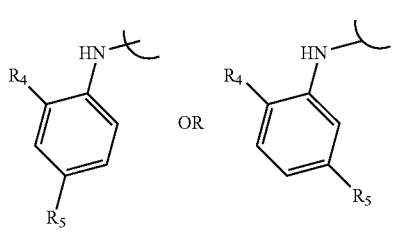

wherein $R_4$ and $R_5$ are, each independently, halogen, nitro, cyano, a group —O—$R_3$, —O—CO—$R_3$, —CO—O—$R_3$, —N—($R_3$)$_2$, —N($R_3$)—CO—$R_3$, —CO—N($R_3$)$_2$, —N($R_3$)CON($R_3$)$_2$, —CO—$R_3$, —S—$R_3$, —S(O)$_2$—$R_3$, or an optionally substituted group selected from straight or branched $C_1$-$C_6$ alkyl, polyfluorinated alkyl, polyfluorinated alkoxy, $C_3$-$C_6$ cycloalkyl, $C_2$-$C_6$ alkenyl, $C_2$-$C_6$ alkynyl, heterocyclyl, heterocyclylalkyl, aryl, arylalkyl, heteroaryl, heteroarylalkyl and hydroxyalkyl, wherein $R_3$ is as defined above;

A particularly preferred class of compounds of formula (I) are the compounds wherein:
$R_1$ and $R_2$ taken together are a —NH—CH$_2$—CH$_2$— chain and form a 6-membered lactam fused with the pyrrole ring, and $R_3$, $R_4$ and $R_5$ are as defined above.

Preferred specific compounds of formula (I) are the compounds listed below (for the meaning of the codes, see the Examples section):
1) 5-[2-(5-bromo-2-trifluoromethoxy-phenylamino)-pyrimidin-4-yl]-1-methyl-1H-pyrrole-3-carboxylic acid ethyl ester (A1B1C1M1);
2) 5-[2-(5-bromo-2-methyl-phenylamino)-pyrimidin-4-yl]-1-methyl-1H-pyrrole-3-carboxylic acid (A1B2C1M1);
3) 5-[2-(5-bromo-2-trifluoromethoxy-phenylamino)-pyrimidin-4-yl]-1-methyl-1H-pyrrole-3-carboxylic acid amide (A1B3C1M1);
4) 1-methyl-5-[2-(5-piperazin-1-yl-2-trifluoromethoxy-phenylamino)-pyrimidin-4-yl]-1H-pyrrole-3-carboxylic acid amide (A1B3C2M1);
5) 1-methyl-5-{2-[5-(4-methyl-piperazin-1-yl)-2-trifluoromethoxy-phenylamino]-pyrimidin-4-yl}-1H-pyrrole-3-carboxylic acid ethyl ester (A1B1C3M1);
6) 1-methyl-5-{2-[5-(4-methyl-piperazin-1-yl)-2-trifluoromethoxy-phenylamino]-pyrimidin-4-yl}-1H-pyrrole-3-carboxylic acid (A1B2C3M1);
7) 1-methyl-5-{2-[5-(4-methyl-piperazin-1-yl)-2-trifluoromethoxy-phenylamino]-pyrimidin-4-yl}-1H-pyrrole-3-carboxylic acid amide (A1B3C3M1);
8) 5-[2-(5-bromo-2-trifluoromethoxy-phenylamino)-pyrimidin-4-yl]-1-(2-fluoro-ethyl)-1H-pyrrole-3-carboxylic acid ethyl ester (A2B1C1M1);
9) 5-[2-(5-bromo-2-trifluoromethoxy-phenylamino)-pyrimidin-4-yl]-1-(2,2,2-trifluoro-ethyl)-1H-pyrrole-3-carboxylic acid ethyl ester (A3B1C1M1);
10) 5-[2-(5-bromo-2-trifluoromethoxy-phenylamino)-pyrimidin-4-yl]-1-(2-fluoro-ethyl)-1H-pyrrole-3-carboxylic acid amide (A2B3C1M1);
11) 5-{2-[5-(4-methyl-piperazin-1-yl)-2-trifluoromethoxy-phenylamino]-pyrimidin-4-yl}-1-(2,2,2-trifluoro-ethyl)-1H-pyrrole-3-carboxylic acid ethyl ester (A3B1C3M1);
12) 5-{2-[5-(4-methyl-piperazin-1-yl)-2-trifluoromethoxy-phenylamino]-pyrimidin-4-yl}-1-(2,2,2-trifluoro-ethyl)-1H-pyrrole-3-carboxylic acid (A3B2C3M1);
13) 5-[2-(5-bromo-2-trifluoromethoxy-phenylamino)-pyrimidin-4-yl]-1-(2,2,2-trifluoro-ethyl)-1H-pyrrole-3-carboxylic acid amide (A3B3C1M1);
14) 5-{2-[5-(4-methyl-piperazin-1-yl)-2-trifluoromethoxy-phenylamino]-pyrimidin-4-yl}-1-(2,2,2-trifluoro-ethyl)-1H-pyrrole-3-carboxylic acid amide (A3B3C3M1);
15) 1-methyl-2-{2-[5-(4-methyl-piperazin-1-yl)-2-trifluoromethoxy-phenylamino]-pyrimidin-4-yl}-1,5,6,7-tetrahydro-pyrrolo[3,2-c]pyridin-4-one (A1C3M2);
16) 2-{2-[5-(4-methyl-piperazin-1-yl)-2-trifluoromethoxy-phenylamino]-pyrimidin-4-yl}-1-(2,2,2-trifluoro-ethyl)-1,5,6,7-tetrahydro-pyrrolo[3,2-c]pyridin-4-one (A3C3M2), and
17) 1-(2-Hydroxy-ethyl)-2-{2-[5-(4-methyl-piperazin-1-yl)-2-trifluoromethoxy-phenylamino]-pyrimidin-4-yl}-1,5,6,7-tetrahydro-pyrrolo[3,2-c]pyridin-4-one (A5C3M2).

The present invention also provides a process for the preparation of a compound of formula (I) as defined above, characterized in that the process comprises:
d) deprotecting a compound of formula (XIII):

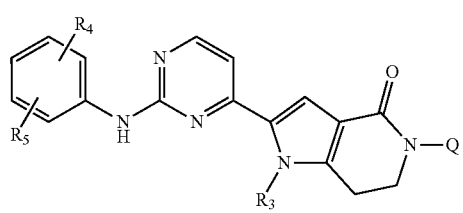

(XIII)

wherein $R_3$, $R_4$ and $R_5$ are as defined above and Q is a suitable protecting amino group such as t-butoxycarbonyl, to give a compound of formula (Ia):

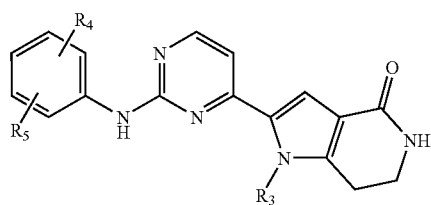

(Ia)

wherein $R_3$, $R_4$ and $R_5$ are as defined above; or
d') reacting a compound of formula (VIII):

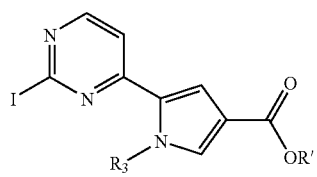

(VIII)

wherein R' is as defined above except hydrogen and $R_3$ is as defined above, with an optionally substituted arylamine of formula (IX):

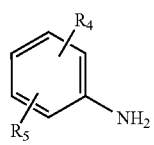

(IX)

wherein $R_4$ and $R_5$ are as defined above, under reductive conditions, to give a compound of formula (Ib):

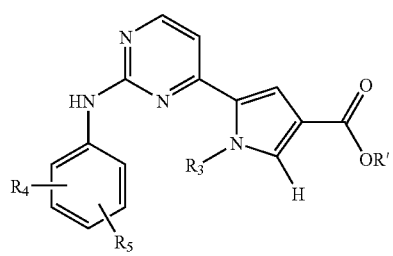

(Ib)

wherein R' is as defined above except hydrogen and $R_3$, $R_4$ and $R_5$ are as defined above; or
d") reacting a compound of formula (VII):

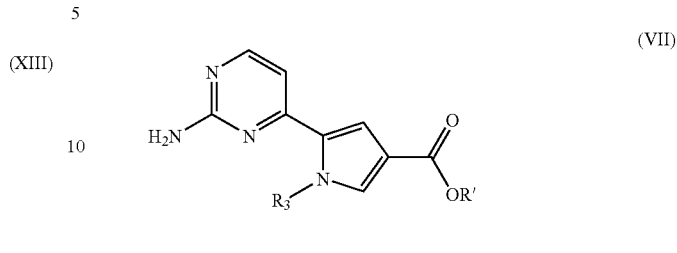

(VII)

wherein R' is as defined above except hydrogen and $R_3$ is as defined above, with an optionally substituted iodophenyl derivative of formula (XVII):

(XVII)

wherein $R_4$ and $R_5$ are as defined above, under reductive conditions, to give a compound of formula (Ib) as defined above;
optionally separating the resulting compound into the single isomers, converting the compound into a different compound of formula (I), and/or into a pharmaceutically acceptable salt if desired.

The present invention further provides a process for the preparation of a compound of formula (Ia) as defined above, characterized in that the compound of formula (XIII) as defined above, is prepared according to the following steps:
a) reacting a compound of formula (XIV):

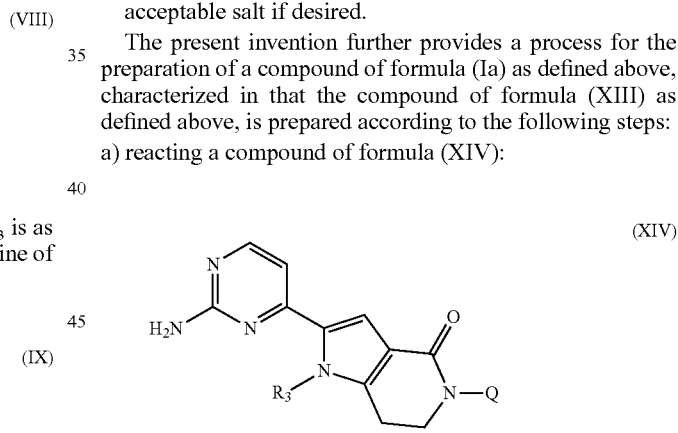

(XIV)

wherein $R_3$ is as defined above, with isoamyl nitrite in presence of a iodide source e.g. copper iodide, cesium iodide, iodine or a mixture of them, to give a compound of formula (XV):

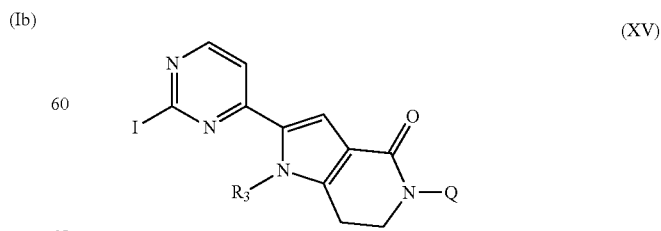

(XV)

wherein $R_3$ and Q are as defined above;

b) reacting the resulting compound of formula (XV) with an optionally substituted arylamine of formula (IX) as defined above, under reductive conditions, to give a compound of formula (XIII) as defined above; or
c) reacting a compound of formula (XIV) as defined above, with an optionally substituted iodophenyl derivative of formula (XVII) as defined above, under reductive conditions, to give a compound of formula (XIII) as defined above.

The present invention further provides a process for the preparation of a compound of formula (Ib) as defined above, characterized in that the compound of formula (VII) and (VIII) as defined above, are prepared according to the following steps:

e) reacting the compound of formula (II):

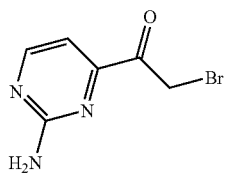

(II)

with a compound of formula (X):

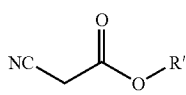

(X)

wherein R' is as above defined except hydrogen, in presence of sodium metal, to give a compound of formula (III):

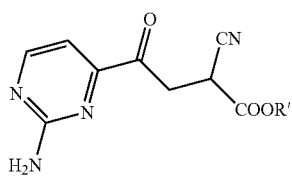

(III)

wherein R' is as above defined except hydrogen;

f) reacting the resulting compound of formula (III) with hydrochloric or hydrobromic acid, to give a compound of formula (IV):

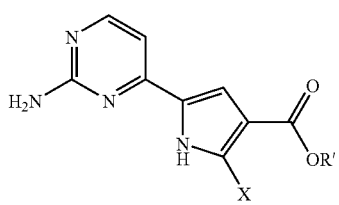

(IV)

wherein R' is as above defined except hydrogen and X is chlorine or bromine;

g) reducing the resulting compound of formula (IV), to give a compound of formula (V):

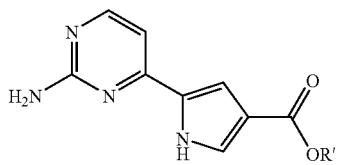

(V)

wherein R' is as above defined except hydrogen;

h) reacting the resulting compound of formula (V) with a compound of formula (VI):

$$R_3\text{—}Y \quad (VI)$$

wherein $R_3$ is as defined above and Y is halogen or a suitable leaving group such as toluensulfonyl or trifluoromethanesulfonyl in the presence of a base, to give a compound of formula (VII) as defined above;

i) reacting the resulting compound of formula (VII) with isoamyl nitrite in presence of a iodide source such as copper (I) iodide, cesium iodide, iodine or a mixture of them, to give a compound of formula (VIII) as defined above.

A compound of formula (I) may be converted into another compound of formula (I), said conversion is carried out by one or more of the following reactions:

I) converting a compound of formula (Ib) as defined above, into a compound of formula (I) wherein $R_1$ is a group —OH or corresponding salt through acidic or basic hydrolysis;

II) converting a compound of formula (Ib) as defined above, into a compound of formula (I) wherein $R_1$ is a group —NR'R" by treatment with an amine of formula R'R"—NH (XII), as defined above, in a sealed tube;

III) converting a compound of formula (I) wherein $R_1$ is —OH or corresponding salt into a compounds of formula (I) wherein $R_1$ is a group —NR'R", through reaction with an amine of formula R'R"—NH (XII), wherein R' and R" are as defined above, under basic conditions and in the presence of a suitable condensing agent;

IV) converting a compound of formula (I) wherein $R_1$ is —NR'R" and $R_5$ is bromine, into a compound of formula (I) wherein $R_1$ is as defined above and $R_5$ is heterocyclyl or a group —N—$(R_3)_2$, wherein $R_3$ is as defined above, under reductive conditions, by treatment with an amine of formula R'''R'''—NH (XI) wherein R''' and R''' are, each independently, hydrogen or an optionally substituted group selected from straight or branched $C_1$-$C_6$ alkyl, $C_2$-$C_6$ alkenyl, $C_2$-$C_6$ alkynyl, $C_3$-$C_6$ cycloalkyl and heterocyclyl, or R''' and R''' taken together with the nitrogen atom to which they are bonded, may form an optionally substituted heterocyclyl group.

V) converting a compound of formula (Ia) wherein $R_5$ is bromine, into a compound of formula (Ia) wherein $R_5$ is heterocyclyl or a group —N—$(R_3)_2$, wherein $R_3$ is as defined above, by treatment with an amine of formula R'''R'''—NH (XI) as defined above, under reductive conditions.

A compound of formula (XIII) wherein $R_5$ is bromine, may be converted into a compound of formula (XIII) wherein $R_5$ is heterocyclyl or a group —N—$(R_3)_2$, wherein $R_3$ is as defined above, as described above in conversion V.

The above process, in any one of the aforementioned variants, is an analogy process which can be carried out according to well known methods known in the art.

According to the step (d) of the process, the deprotection of the compound of formula (XIII) can be accomplished in a variety of ways according to conventional methods well known in the art (Green, Theodora W. and Wuts, Peter G. M.—*Protective Groups in Organic Synthesis, Third Edition*, John Wiley & Sons Inc., New York (N.Y.), 1999).

Preferably, when Q is a t-butoxycarbonyl residue is carried out in a suitable solvent such as dichloromethane or dioxane and in the presence of catalytic amounts of an acid such as hydrochloric acid or trifluoroacetic at a temperature ranging from room temperature to 90° C. and for a time ranging from about 1 to about 24 hours.

According to the step (d') of the process, the reaction of a compound of formula (VIII) with a compound of formula (IX) can be accomplished in a variety of ways according to conventional methods. Preferably it is carried out in a suitable solvent such as dimethylformamide, dimethoxyethane or dimethylacetamide and in the presence of catalytic amounts of palladium acetate, (2,2'-bis(diphenylphosphino)-1,1'-binaphtalene (BINAP) and a base such as potassium carbonate, potassium phosphate or cesium carbonate, at a temperature ranging from room temperature to 150° C. and for a time ranging from about 2 to about 24 hours.

According to step (d") of the process, the reaction of a compound of formula (VII) with compound of formula (XVII) can be accomplished in a variety of ways according to conventional methods. Preferably it is carried out in a suitable solvent such as dimethylformamide, dimethoxyethane or preferably dioxane and in the presence of catalytic amounts of tris(dibenzylidene-acetone)dipalladium(0), 4,5-bis(diphenylphosphino)-9,9-dimethylxanthene (XANTPHOS)) and a base such as potassium carbonate, potassium phosphate or cesium carbonate, at a temperature ranging from room temperature 70° C. to 110° C. and for a time ranging from about 2 to about 24 hours.

According to step (a) of the process, the reaction of the compound of formula (XIV) with isoamyl nitrite in presence of a iodide source can be accomplished in a variety of ways according to conventional methods. Preferably it is carried out in presence of cesium iodide, copper iodide or iodine. The reaction is carried out preferably in a solvent such as, for instance, 1,2-dimethoxyethane, at a temperature ranging from 50° C. to about 80° C., and for a time of about 2 to about 24 hours.

According to step (b) of the process, the reaction of the compound of formula (XV) with a compound of formula (IX) can be accomplished in a variety of ways according to conventional methods. Preferably it is carried out as described in (d').

According to step (c) of the process, the reaction of a compound of formula (XIV) with a compound of formula (XVII) can be accomplished in a variety of ways according to conventional methods. Preferably it is carried out as described in (d").

According to step (e) of the process, the reaction of a compound of formula (II) with a compound of formula (X), can be accomplished in a variety of ways according to conventional methods. Preferably it is carried out by reaction with ethyl cyanoacetate and sodium metal in presence of N,N-diisopropylethylamine. The reaction is carried out in a suitable solvent such as dichloromethane or tetrahydrofuran, at a temperature ranging from room temperature to about 50° C., and for a time of about 2 to about 48 hours.

According to step (f) of the process, the reaction of a compound of formula (III) with hydrochloric or hydrobromic acid, can be accomplished in a variety of ways according to conventional methods. Preferably it is carried out in a suitable solvent such as diethyl ether, dichloromethane or tetrahydrofuran, at a temperature ranging from −5° C. to about 50° C., and for a time of about 1 to about 48 hours.

According to step (g) of the process, the reduction of a compound of formula (IV), can be accomplished in a variety of ways according to conventional methods. Preferably it is carried out with ammonium formate in the presence of catalytic amount of 10% Pd/charcoal. The reaction is preferably carried out at reflux in ethanol as solvent and for a time of about 2 to about 48 hours.

According to step (h) of the process, the reaction of a compound of formula (V) with a compound of formula (VI), can be accomplished in a variety of ways according to conventional methods. Preferably it is carried out in the presence of a suitable base as such as cesium carbonate and in a solvent such as, for instance, dimethylformamide, at a temperature ranging from room temperature to about 80° C., and for a time of about 2 to about 48 hours.

According to step (i) of the process, the reaction of a compound of formula (VII) with isoamyl nitrite and a iodide source can be accomplished in a variety of ways according to conventional methods. Preferably it is carried out as described in (a).

According to conversion (I) of the process, the conversion of a compound of formula (Ib) as defined above into a compound of formula (I) wherein $R_1$ is a group —OH or corresponding salt, can be accomplished in a variety of ways according to conventional methods. Preferably it is carried in a suitable solvent such as a methanol or ethanol with a base such as sodium hydroxide or potassium hydroxide, at a temperature ranging from about 25° C. to about 100° C. and for a time ranging from about 2 to about 24 hours.

According to conversion (II) of the process, the conversion of a compound of formula (Ib) as defined above into a compound of formula (I) wherein $R_1$ is a group —NR'R", can be accomplished in a variety of ways according to conventional methods. Preferably it is carried in a suitable solvent such as a methanol or dimethylformamide or mixtures thereof with ammonium hydroxide mixture, at a temperature ranging from about 50° C. to about 150° C. and for a time ranging from about 2 to about 24 hours.

According to conversion (III) of the process, the conversion of a compound of formula (I) wherein $R_1$ is —OH or corresponding salt into a compounds of formula (I) wherein $R_1$ is a group —NR'R", can be accomplished in a variety of ways according to conventional methods. Preferably it is carried in the presence of an amine of formula (XII), under basic conditions, preferably with N,N-diisopropyl-N-ethylamine or triethylamine, in a suitable solvent such as dichloromethane, dimethylformamide, tetrahydrofuran, or dioxane, and in the presence of a suitable condensing agent such as N,N'-dicyclohexylcarbodiimide (DCC), N-(3-dimethylaminopropyl)-N'-ethylcarbodiimide hydrochloride (EDCI) or O-(benzotriazol-1-yl)-N,N,N',N'-tetramethylisouronium tetrafluoroborate (TBTU); catalytic amounts of (benzotriazol-1-yloxy)tripyrrolidinophosphonium hexafluorophosphate (PyBOP) or N-hydroxybenzotriazole may be also required.

According to conversion (IV) of the process, the conversion of a compound of formula (I) wherein $R_1$ is —NR'R" and $R_5$ is bromine into a compound of formula (I) wherein R1 is as defined above and $R_5$ is heterocyclyl or a group —N—$(R_3)_2$, wherein $R_3$ is as defined above, can be accomplished in a variety of ways according to conventional methods. Preferably it is carried in a suitable solvent such as tetrahydrofurane or dioxane by treatment with an amine of formula (XI) and in the presence of catalytic amounts of tris(dibenzylideneacetone)dipalladium, 2-dicyclohexylphosphino-2'-(N,N-dimethylamino)-biphenyl) and a base such as lithium bis(trimethylsilyl)amide, at a temperature ranging from room temperature to reflux and for a time ranging from about 1 to about 24 hours.

According to conversion (V) of the process, the conversion of a compound of formula (Ia) or (XIII) wherein $R_5$ is bromine, into a compound of formula (Ia) or (XIII) wherein $R_5$ is heterocyclyl or a group —N—$(R_3)_2$, wherein $R_3$ is as defined above, can be accomplished in a variety of ways according to conventional methods. Preferably it is carried out as described in conversion (IV).

It is known to the skilled person that transformation of a chemical function into another may require that one or more reactive centers in the compound containing this function be protected in order to avoid undesired side reactions. Protection of such reactive centers, and subsequent deprotection at the end of the synthetic transformations, can be accomplished following standard procedures described, for instance, in: Green, Theodora W. and Wuts, Peter G. M.—Protective Groups in Organic Synthesis, Third Edition, John Wiley & Sons Inc., New York (N.Y.), 1999.

In cases where a compound of formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wilen, Samuel H.,—Enantiomers, Racemates, and Resolutions, John Wiley & Sons Inc., New York (N.Y.), 1981.

A compound of formula (I) can also be transformed into a pharmaceutically acceptable salt according to standard procedures that are known to those skilled in the art. Alternatively, a compound of formula (I) that is obtained as a salt can be transformed into the free base or the free acid according to standard procedures that are known to the skilled person.

According to any variant of the process for preparing the compounds of formula (I), the starting materials and any other reactants are known or easily prepared according to known methods.

For example, the compound of formula (XIV) can be prepared as described in the aforementioned WO 2005/014572.

Compounds of formula (II), (VI), (X), (XI) and (XII) are commercially available.

Some compounds of formula (IX) and (XVII) are commercially available, others have been prepared following known procedures, see the following example 6.

Another object of the present invention is to provide an intermediate of formula (XV):

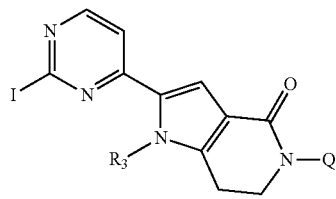

(XV)

wherein $R_3$ and Q are as defined above, and an intermediate of formula (VIII):

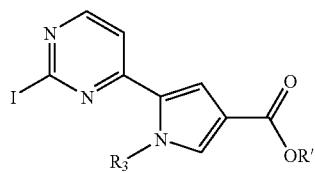

(VIII)

wherein R' is as defined above except hydrogen and $R_3$ is as defined above.

Pharmacology

The compounds of formula (I) are active as protein kinase inhibitors and are therefore useful, for instance, to restrict the unregulated proliferation of tumor cells.

In therapy, they may be used in the treatment of various tumors, such as those formerly defined, as well as in the treatment of other cell proliferative disorders such as benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The inhibiting activity of putative PLK-1 inhibitors and the potency of selected compounds was determined through the assay described below.

The short forms and abbreviations used herein have the following meaning:
Ci Curie
DMSO dimethylsulfoxide
KDa kiloDalton
microCi microCurie
mg milligram
microg microgram
ng nanogram
L liter
mL milliliter
microL microliter
M molar
mM millimolar
microM micromolar
nM nanomolar
Cloning, Expression and Purification of Recombinant PLK1 Kinase Domain.

PLK1 kinase domain (corresponding to residues 2-345) was PCR amplified from the full-length human PLK1 gene obtained from Incyte as clone 3180142.

Amplification was performed using the forward oligonucleotide:

[SEQ ID NO: 1]
5'GGGGACAAGTTTGTACAAAAAAGCAGGCTTATTCGAAAACCTGTATTT

TCAGGGCCCTAGTGCTGCAGTGACTGCAGGGAAG3' and the reverse oligonucleotide:

[SEQ ID NO: 2]
5'GGGGACCACTTTGTACAAGAAAGCTGGGTTTCACTATTTATTGAGGAC

TGTGAGGGGCTT-3'.

For cloning purposes, the oligonucleotides included attB sites in order to obtain an attB-flanked PCR product suitable for cloning using the Gateway® technology (Invitrogen). Furthermore, for purification purposes, forward primer included a TEV® cleavage site (Amersham Biosciences). The resulting PCR product was cloned in the pDONR221 plasmid and then transferred in the baculovirus expression vector pVL1393 (Invitrogen) Gateway®-modified. For expression and purification purposes, a His tag was added N-terminal to the PLK kinase domain. Cloning was performed according to the protocols described in the Gateway® manual.

Baculoviruses were generated by cotransfecting Sf9 insect cells with the expression vector and the viral DNA using the BaculoGold® transfection kit (Pharmingen). Viral supernatant was recovered after 5 days and subjected to 3 rounds of amplification to increase viral titer. Recombinant protein was produced by infecting High5 insect cells. After 48 hours of infection, cells were recovered, pelletted and freezed at −80° C. For purification of recombinant protein, pellet was thawed, resuspended in lysis buffer (PBS, NaCl 150 mM, CHAPS 0.1%, DTT 20 mM, glycerol 10%, protease inhibitors) and lysed by sonication. Lysate was cleared by centrifugation and loaded on a Nichel affinity column. After extensive wash, recombinant protein was cleaved and eluted by incubation with TEV® protease.

Biochemical Assay for Inhibitors of PLK-1 Kinase Activity

The inhibitory activity of putative kinase inhibitors and the potency of selected compounds were determined using a trans-phosphorylation assay.

In the bioassay, PLK1 enzyme KD (Kinase Domain) 2-345 expressed in insect cells was used, see Swissprot No. P53350.

Specific peptide or protein substrates are trans-phosphorylated by their specific serine-threonine or tyrosine kinase, in the presence of ATP traced with $^{33}$P-γ-ATP, and in the presence of their own optimal buffer and cofactors.

At the end of the phosphorylation reaction, more than 98% cold ATP and radioactive ATP is captured by an excess of the ion exchange dowex resin; the resin then settles down to the bottom of the reaction plate by gravity.

Supernatant, containing the phosphorylated substrate, is subsequently withdrawn and transferred into a counting plate, then evaluated by β-counting.

Reagents/Assay Conditions i. Dowex Resin Preparation 500 g of wet resin (SIGMA, custom prepared resin DOWEX 1×8 200-400 mesh, 2.5 Kg) are weighed out and diluted to 2 L in 150 mM sodium formate, pH 3.00.

The resin is allowed to settle down (some hours) and then the supernatant is discarded. After three washes as above over a couple of days, the resin is allowed to settle, the supernatant is discarded and two volumes of 150 mM sodium formate buffer are added per volume of pellet. The pH is then measured and should be around 3.00. The washed resin is stable for more than one week; the stock resin is kept at 4° C. before use.

ii. Kinase Buffer (KB)

Kinase buffer was composed of 50 mM HEPES pH 7.9 containing 10 mM $MnCl_2$, 1 mM DTT, 3 microM $NaVO_3$, and 0.2 mg/mL BSA, 10 mM β-glycerophosphate.

iii Assay Conditions

The kinase assay was run with a final enzyme concentration PLK-1 (PLK1 KD 2-345), of 3 nM in presence of 40 microM ATP, 3 nM $^{33}$P-γ-ATP and 85 microM substrate alpha-casein, SIGMA, #C-3240.

Robotized Dowex Assay 1) 3× Enzyme mix (done in Kinase Buffer 3×), 5 microL/well
2) 3× substrate and ATP mix (done in $ddH_2O$), together with $^{33}$P-γ-ATP, 5 microL/well
3) 3× test compounds (diluted into $ddH_2O$—3% DMSO)—5 microL/well Compound Dilution and Assay Scheme is Defined Below.

i. Dilution of Compounds 10 mM stock solutions of test compounds in 100% DMSO were distributed into 96 well 12×8 format microtiter plates.

For % inhibition studies, individual dilution plates at 1 mM, 100 microM and 10 microM are prepared in 100% DMSO, then diluted at a 3× concentration (30, 3 and 0.3 microM) in $ddH_2O$, 3% DMSO. A Multimek 96 (Beckman) is used for dilutions and compound pipetting into the test plates For $IC_{50}$ determination, compounds are received as 1 mM, 100% DMSO solutions, plated into the first column of a microtiter plate (A1 to G1), 100 microL.

A Biomek 2000 (Beckman) is used for serial 1:3 dilutions in water, 3% DMSO, from column A1 to A10 and for all the seven compounds in the plate. In a standard experiment, the highest concentration of all compounds is 30 microM, then diluted in the final test mixture down to 10 microM.

ii. Assay Scheme 384-well plates, V bottom (test plates) are prepared with 5 microL of the compound dilution (3×) and then placed onto a PlateTrak 12 robotized station (Perkin Elmer; the robot has one 384-tips pipetting head for starting the assay plus one 96-tips head for dispensing the resin) together with one reservoir for the Enzyme mix (3×) and one for the ATP mix (3×). At the start of the run, the robot aspirates 5 microL of ATP mix, makes an air gap inside the tips (3 microL) and aspirates 5 microL of PLK1 mix. The following dispensation into the plates allows the kinase reaction to start upon 3 cycles of mixing, done by the robot itself.

At this point, the correct concentration is restored for all reagents.

The robot incubates the plates for 60 minutes at room temperature, and then stops the reaction by pipetting 70 microL of dowex resin suspension into the reaction mix. Three cycles of mixing are done immediately after the addition of the resin.

Another mixing cycle is performed after all the plates are stopped, this time using normal tips: the plates are then allowed to rest for about one hour in order to maximize ATP capture. At this point, 20 microL of the supernatant are transferred into 384-Optiplates (Perkin-Elmer), with 70 microL of Microscint 40 (Perkin-Elmer); after 5 min of orbital shaking the plates are read on a Perkin-Elmer Top Count radioactivity counter.

iii. Data Analysis

Data are analysed by an internally customized version of the SW package "Assay Explorer" that provides either % inhibition for primary assays or sigmoidal fittings of the ten-dilutions curves for $IC_{50}$ determination, for the secondary assays/hit confirmation routines.

Biochemical Assay for Inhibitors of Aurora-2 Kinase Activity

The in vitro kinase inhibition assay was conducted in the same way as described for PLK-1 enzyme.

i. Kinase Buffer (KB) for Aurora-2

The kinase buffer was composed of 50 mM HEPES, pH 7.0, 10 mM $MnCl_2$, 1 mM DTT, 3 microM $NaVO_3$, and 0.2 mg/mL BSA.

ii. Assay Conditions for Aurora-2 (Final Concentrations)

The kinase assay was run with an enzyme concentration of 2.5 nM, 10 microM ATP, 1 nM $^{33}$P-γ-ATP, and 8 microM substrate, composed of 4 LRRWSLG repeats.

Inhibition Assay of Cdk2/Cyclin A Activity

Kinase reaction: 1.5 microM histone H1 substrate, 25 microM ATP (0.2 microCi P33γ-ATP), 30 ng of baculovirus co-expressed Cdk2/Cyclin A, 10 microM inhibitor in a final volume of 100 microL buffer (TRIS HCl 10 mM pH 7.5, $MgCl_2$ 10 mM, 7.5 mM DTT) were added to each well of a 96 U bottom well plate. After 10 min at 37° C. incubation, reaction was stopped by 20 microL EDTA 120 mM.

Capture: 100 microL were transferred from each well to MultiScreen plate, to allow substrate binding to phosphocellulose filter. Plates were then washed 3 times with 150 microL/well PBS $Ca^{++}/Mg^{++}$ free and filtered by Multi-Screen filtration system.

Inhibition Assay of Cdc7 Activity

The inhibition assay of Cdc7/Dbf4 activity was performed in 96 wells plate according to the following protocol.

To each well of the plate were added:
  10 microL test compound (10 increasing concentrations in the nM to uM range to generate a dose-response curve). The solvent for test compounds contained 3% DMSO. (final concentration 1%)

10 microL substrate MCM2 (6 microM final concentration), a mixture of cold ATP (2 microM final concentration) and radioactive ATP (1/5000 molar ratio with cold ATP).

10 microL enzyme (Cdc7/Dbf4, 2 nM final concentration) that started the reaction. The buffer of the reaction consisted in 50 mM HEPES pH 7.9 containing 15 mM MgCl$_2$, 2 mM DTT, 3 uM NaVO$_3$, 2 mM glycerophosphate and 0.2 mg/ml BSA.

After incubation for 60 minutes at room temperature, the reaction was stopped by adding to each well 150 microL of Dowex resin in the presence of 150 mM formic acid.

After another 60 min incubation, 50 microL of suspension were withdrawn and transferred into 96-well OPTIPLATEs containing 150 microl of MicroScint 40 (Packard); after 5-10 minutes shaking the plates were read for 1 min in a Packard TOP-Count radioactivity reader.

IC50 determination: inhibitors were tested at different concentrations ranging from 0.0005 to 10 microM. Data are analysed by an internally customized version of the SW package "Assay Explorer"

In vitro Cell Proliferation Assay

A2780 human ovarian and MCF7 human breast cancer cells (1250 cells/well) were seeded in white 384well-plates in complete medium (RPMI1640 or EMEM plus 10% Fetal bovine serum) and treated with compounds dissolved in 0.1% DMSO, 24 h after seeding. The cells were incubated at 37° C. and 5% CO$_2$ and after 72 hours the plates were processed using CellTiter-Glo assay (Promega) following the manufacturer's instruction.

CellTiter-Glo is a homogenous method based on the quantification of the ATP present, an indicator of metabolitically active cells. ATP is quantified using a system based on luciferase and D-luciferin resulting into light generation. The luminescent signal is proportional to the number of cells present in culture.

Briefly 25 microL/well reagent solution are added to each wells and after 5 minutes shacking microplates are red by a luminometer. The luminescent signal is proportional to the number of cells present in culture.

Given the above inhibition assays, the compounds of formula (I) of the invention resulted to possess a remarkable PLK inhibitory activity, typically with IC$_{50}$ lower than 0.1 microM. See, as an example, the following experimental data (IC$_{50}$) of one representative compounds of the invention of formula (I) in comparison with the closest compound of the prior art, described in WO 2005/014572.

Reference Compound: PLK1 IC$_{50}$=0.11 microM
Compound A1C3M2: PLK1 IC$_{50}$=0.009 microM Reference compound

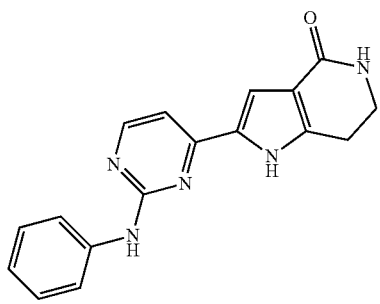

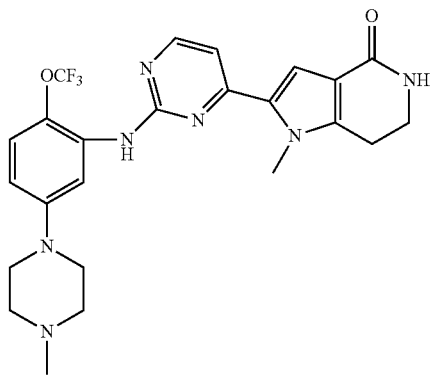

A1C3M2

Surprisingly, the PLK-1 inhibitory activity of Compound A1C3M2 resulted to be markedly superior to that of the reference compound.

So far, the novel compounds of the invention are unexpectedly endowed with a PLK-1 inhibitory activity significantly higher than that of the structurally closest compounds of the prior art and are thus particularly advantageous in therapy of diseases caused by dysregulated protein kinase activity such as cancer.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine, methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

EXAMPLES

Before taking into consideration the synthetic preparation of the specific compounds of formula (I) of the invention, for instance as defined in the following examples, attention should be given to the fact that all the compounds are conveniently and unambiguously identified through a coding system (see following table IV), some of them are herewith listed and indicated according to their chemical name.

Each code, which unambiguously identifies a single specific compound of formula (I), consists of four units A-B-C-M1 or three units A-C-M2.

Code A represents any substituent, as per formula (I), being attached to the rest of the molecule to the pyrrolo nitrogen atom. Each A group is represented through the proper chemical formula in the following table I, also indicating its point of attachment to the rest of the molecule.

Code B represents any substituent, as per formula (I), being attached to the rest of the molecule to the position 3, as per formula (I). Each B group is represented through the proper chemical formula in the following table II, also indicating its point of attachment to the rest of the molecule.

Code C represents any group, as per formula (I), being attached to the rest of the molecule to the position 2 of the pyrimidine ring. Each C group is represented through the proper chemical formula in the following table III, also indicating its point of attachment to the rest of the molecule.

Each specific A, B and C group is represented and consecutively numbered in the following table I, II and III respectively.

Finally, code M1 refers to the central core of the molecule (I) while code M2 refers to the central core of the molecule (Ia).

Therefore, the coding system presently used for some compounds of formula (I) or (Ia) can be shortly summarised as follows:

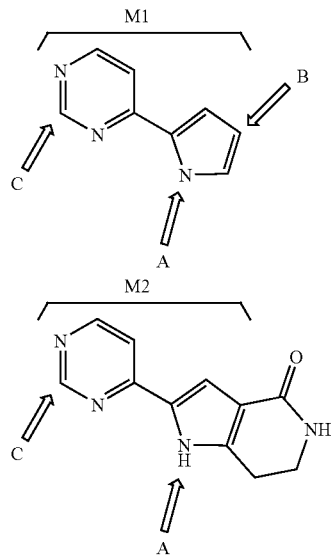

Just as examples, which are not intended to limit the scope of the present invention, the compound A1B1C1M1 (see example) represents the pyrrolo-pyrimidine derivative of formula (I) wherein the central core is represented by the moiety M1, substituted by the group A1, B1 and C1, so identifying the structure reported below:

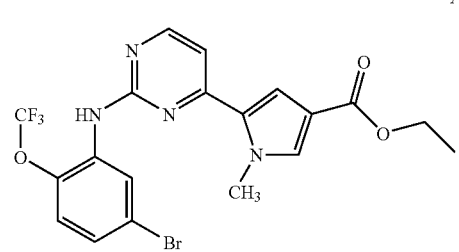

A1B1C1M1 and the compound A1C3M2 (see example) represents the pyrrolo-pyrimidine derivative of formula (Ia) wherein the central core is represented by the moiety M2, substituted by the group A1 and C3, so identifying the structure reported below:

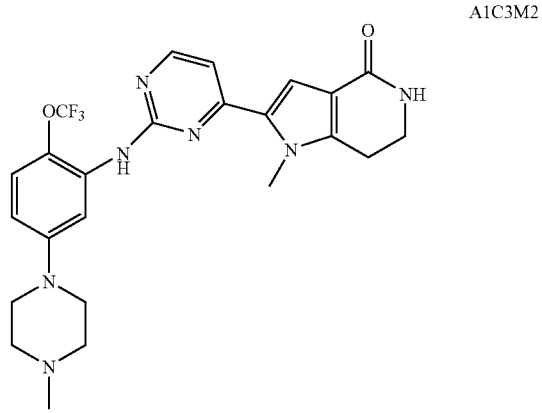 [SMILES: CN1CCN(c2ccc(OC(F)(F)F)c(Nc3nccc(-c4cc5c(n4C)CCNC5=O)n3)c2)CC1]

A1C3M2

TABLE I

| Code | A |
|---|---|
| A1 | H₃C—M |
| A2 | F—CH₂—CH₂—M |
| A3 | F₃C—CH₂—M |
| A4 | M—CH₂=CH₂ |
| A5 | M—CH2—CH2—OH |

TABLE II

| Code | B |
|---|---|
| B1 | ethyl ester —C(=O)—O—CH₂CH₃ linked to M |
| B2 | HO—C(=O)—M |
| B3 | H₂N—C(=O)—M |

TABLE III

| Code | C |
|---|---|
| C1 | 2-(OCF₃)-5-bromo-phenyl with NH—M |
| C2 | 2-(OCF₃)-5-(piperazin-1-yl)-phenyl with NH—M |
| C3 | 2-(OCF₃)-5-(4-methylpiperazin-1-yl)-phenyl with NH—M |
| C4 | 2-(OCH₃)-5-(4-methylpiperazin-1-yl)-phenyl with NH—M |
| C5 | 2-(OCF₃)-4-(4-methylpiperazin-1-yl)-phenyl with NH—M |
| C6 | 2-(OCH₃)-4-(4-methylpiperazin-1-yl)-phenyl with NH—M |
| C7 | 2-(OCH₃)-4-[4-(4-methylpiperazin-1-yl)piperidin-1-yl]-phenyl with NH—M |

TABLE IV

| Compound N° | Code |
|---|---|
| 1 | A1B1C1M1 |
| 2 | A1B2C1M1 |
| 3 | A1B3C1M1 |
| 4 | A1B3C2M1 |
| 5 | A1B1C3M1 |
| 6 | A1B2C3M1 |
| 7 | A1B3C3M1 |
| 8 | A2B1C1M1 |
| 9 | A3B1C1M1 |
| 10 | A2B3C1M1 |
| 11 | A3B1C3M1 |
| 12 | A3B2C3M1 |
| 13 | A3B3C1M1 |
| 14 | A3B3C3M1 |
| 15 | A1C3M2 |
| 16 | A3C3M2 |
| 17 | A5C3M2 |
| 18 | A5B3C3M1 |
| 19 | A5C4M2 |

The compounds of the present invention, as prepared according to the following examples, were characterized by $^1$H NMR and by MS analysis.

Example 1

Step (e). 4-(2-amino-pyrimidin-4-yl)-2-cyano-4-oxo-butyric acid ethyl ester

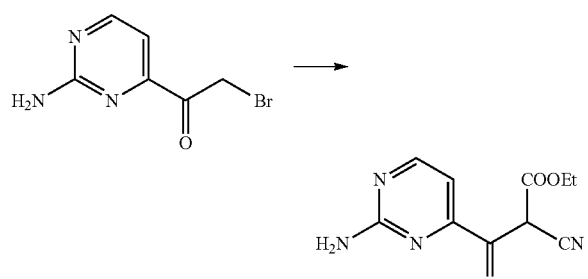

Ethylcyanoacetate (5.3 mL, 0.05 mol) was added to a suspension of sodium metal (1.15 g, 0.05 mol) in 150 mL of anhydrous EtOH at 0° C. After sodium dissolution the reaction mixture was concentrated and the resultant solid was added to a solution of 1-(2-amino-pyrimidin-4-yl)-2-bromo-ethanone (15 g, 0.05 mol) in 300 mL of anhydrous THF and diisopropylethylamine (8.8 mL, 0.05 mol). The reaction mixture was stirred overnight at rt, concentrated and the residue was suspended in water and extracted with DCM. The organic extracts were dried ($Na_2SO_4$) and concentrated. The crude was purified by flash chromatography (DCM/MeOH 95:5) to give 4.5 g (37%) of the title compound as an oil.

$^1$H NMR (400 MHz, DMSO-$d_6$) δ ppm 1.21 (t, J=7.08, 3H), 3.73 (d, J=5.61, 2H), 4.18 (q, J=7.08, 2H), 4.58 (t, J=5.61, 1H), 6.97 (d, J=4.88, 1H), 7.04 (brs, 2H), 8.52 (d, J=4.88, 1H); ESI (+) MS: m/z 249(MH$^+$).

Step (f). 5-(2-amino-pyrimidin-4-yl)-2-bromo-1H-pyrrole-3-carboxylic acid ethyl ester

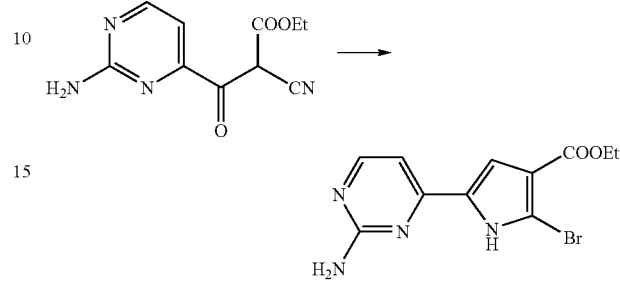

A solution of 4-(2-amino-pyrimidin-4-yl)-2-cyano-4-oxo-butyric acid ethyl ester (364 mg, 1.47 mmol) in anhydrous $Et_2O$ and DCM (1:1 10 mL) was added dropwise to 4.5 mL of 33% HBr in AcOH at 0° C. The mixture was left at 0° C. for 30 min and then at rt until disappearance of the starting material. The solid was filtered, washed with acetone and MeOH, neutralized with 7N $NH_3$ in MeOH to afford 400 mg (88%) of the title compound.

$^1$H NMR (400 MHz, DMSO-$d_6$) δ ppm 1.26 (t, J=7.10, 3H), 4.20 (q, J=7.10, 2H), 6.43 (brs, 2H), 6.99 (d, J=5.24, 1H), 7.23 (s, 1H), 8.23 (d, J=5.24, 1H); ESI (+) MS: m/z 312 (MH$^+$).

According to the same method, but employing the suitable starting material, the following compound was prepared:

5-(2-Amino-pyrimidin-4-yl)-2-chloro-1H-pyrrole-3-carboxylic acid ethyl ester $^1$H NMR (DMSO-$d_6$/400 MHz) δ ppm 1.29 (t, J=7.14, 3H), 4.24 (q, J=7.14, 2H), 6.43 (brs, 2H), 7.36 (d, J=5.24, 1H), 7.59 (s, 1H), 8.34 (d, J=5.24, 1H), 13.52 (brs, 1H); ESI (+) MS: m/z 266 (MH$^+$).

Step (g). 5-(2-amino-pyrimidin-4-yl)-1H-pyrrole-3-carboxylic acid ethyl ester

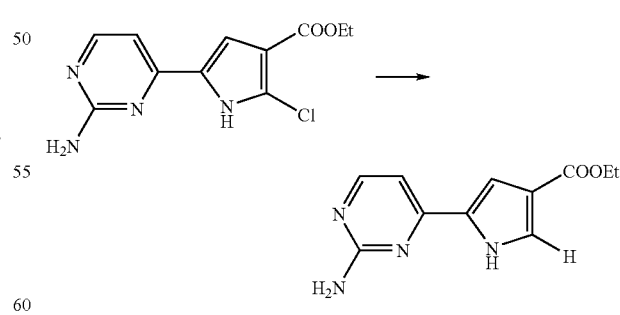

To a suspension of 5-(2-Amino-pyrimidin-4-yl)-2-chloro-1H-pyrrole-3-carboxylic acid ethyl ester hydrochloride (33 g, 0.108 mol) in dry methanol (500 mL), ammonium formate (33 g, 0.523 mol) and 10% Pd/C (3.5 g, 0.0028 mol) were added. The reaction was refluxed for 10 hours. The catalyst was filtered through a pad of Celite rinsing the Celite with dichloromethane (100 mL) and then with methanol (100 mL). The organic fraction was concentrated to small volume (50 mL) diluted with dichloromethane (150 mL) and washed with water (1×200 mL) and the acqueous fraction extracted with dichloromethane (1×200 mL). The organic fractions were combined, dried over sodium sulfate, filtered, and concentered to yield 12.5 g (50%) of the title compound as an light brown solid.

$^1$H NMR (400 MHz, DMSO-$d_6$) δ ppm 1.28 (t, J=7.07 Hz, 3H) 4.21 (q, J=7.07 Hz, 2 H) 6.41 (br. s., 2 H) 6.97 (d, J=5.24 Hz, 1 H) 7.21 (dd, J=2.56, 1.59 Hz, 1 H) 7.48-7.53 (m, 1 H) 8.20 (d, J=5.24 Hz, 1 H) 12.01 (br. s., 1 H); MS (ESI): 233 [M+H]$^+$.

Step (h). 5-(2-amino-pyrimidin-4-yl)-1-methyl-1H-pyrrole-3-carboxylic acid ethyl ester

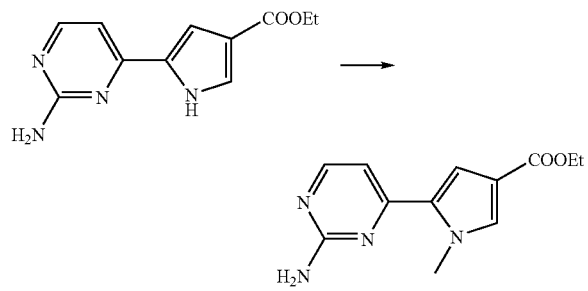

To a solution of 5-(2-amino-pyrimidin-4-yl)-1H-pyrrole-3-carboxylic acid ethyl ester (5.1 g, 21.96 mmol) in tetrahydrofuran (70 mL) and dimethylsulfoxide (15 mL) cooled in a ice-water bath, NaH (0.96 g, 24.15 mmol) and methyl iodide (1.5 mL, 24.15 mmol) were added. The reaction was continued at room temperature for 12 h, the tetrahydrofuran was removed under vacuo, then dichloromethane (200 mL) were added and the organic phase washed with water (100 mL). The acqueous fraction was extracted with dichloromethane (1×100 mL). The organic fractions were combined, dried over sodium sulfate, filtered, and concentered in vacuo. Purification by flash chromatography on silica gel (eluant: dichloromethane/ethanol 95/5) provided 4.45 g (82%) of the title compound as a pale yellow solid.

$^1$H NMR (400 MHz, DMSO-$d_6$) δ ppm 1.23-1.29 (m, 3 H) 4.03 (s, 3 H) 4.19 (q, J=7.11 Hz, 1 H) 6.55 (s, 2 H) 6.91 (d, J=5.37 Hz, 1 H) 7.12 (d, J=1.95 Hz, 1H) 7.61 (d, J=1.46 Hz, 1 H) 8.16 (d, J=5.24 Hz, 1 H); MS (ESI): 247 [M+H]$^+$.

According to the same method, but employing the suitable starting material, the following compounds were prepared:

5-(2-amino-pyrimidin-4-yl)-1-(2-fluoro-ethyl)-1H-pyrrole-3-carboxylic acid ethyl ester $^1$H NMR (400 MHz, DMSO-$d_6$) δ ppm 1.28 (t, J=7.07 Hz, 3 H) 4.22 (q, J=7.07 Hz, 2 H) 4.72 (dt, J=47.80, 4.57 Hz, 2 H) 4.91 (dt, J=27.47, 4.56 Hz, 2 H) 6.58 (s, 2 H) 6.97 (d, J=5.24 Hz, 1 H) 7.23 (d, J=1.95 Hz, 1 H) 7.64 (d, J=1.46 Hz, 1 H) 8.17 (d, J=5.24 Hz, 1 H); MS (ESI): 279 [M+H]$^+$.

5-(2-amino-pyrimidin-4-yl)-1-(2,2,2-trifluoro-ethyl)-1H-pyrrole-3-carboxylic acid ethyl ester $^1$H NMR (400 MHz, DMSO-$d_6$) δ ppm 1.29 (t, J=7.07 Hz, 3 H) 4.23 (q, J=7.15 Hz, 2 H) 5.88 (d, J=9.27 Hz, 2 H) 6.70 (s, 2 H) 6.97 (d, J=5.37 Hz, 1 H) 7.25 (d, J=1.83 Hz, 1 H) 7.74 (d, J=1.10 Hz, 1 H) 8.20 (d, J=5.24 Hz, 1 H); MS (ESI): 315 [M+H]$^+$.

5-(2-amino-pyrimidin-4-yl)-1-[2-(tetrahydro-pyran-2-yloxy)-ethyl]-1H-pyrrole-3-carboxylic acid ethyl ester $^1$H NMR (400 MHz, DMSO-$d_6$) δ ppm 1.27 (t, J=7.07 Hz, 3 H) 3.33-3.48 (m, 4 H) 3.60-3.69 (m, 1 H) 3.77-3.86 (m, 1 H) 4.18-4.25 (m, 2 H) 4.48 (t, J=3.17 Hz, 1 H) 4.82 (t, J=5.24 Hz, 2 H) 6.77 (br. s., 2 H) 7.00 (d, J=5.49 Hz, 1 H) 7.24 (d, J=1.71 Hz, 1 H) 7.66 (d, J=1.95 Hz, 1 H) 8.17 (d, 1 H); MS (ESI): 361 [M+H]$^+$.

Step (i). 5-(2-iodo-pyrimidin-4-yl)-1-methyl-1H-pyrrole-3-carboxylic acid ethyl ester

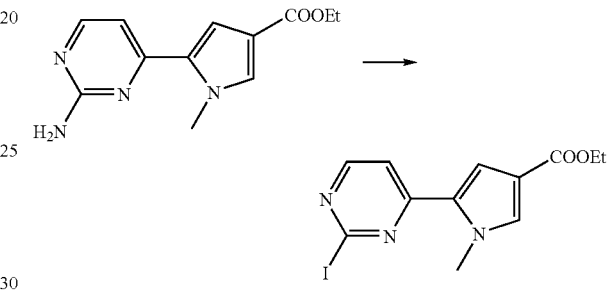

To a well stirred suspension of ethyl 5-(2-amino-pyrimidin-4-yl)-1-methyl-1H-pyrrole-3-carboxylic acid ethyl (4.55 g, 0.018 mol) in dimethoxyethane (200 mL) under $N_2$, cesium iodide (7.04 g, 0.0270 mol), bisublimated iodine (3.42 g, 0.0135 mol), copper iodide (1.54 g, 0.0081 mol) and isopentyl nitrite (5.41 mL, 0.04 mol) were added in sequence. The reaction mixture was stirred vigorously at 65-70° C. for 6 hours. After cooling in a ice-water bath, the solid was filtered off. The filtrate was diluted with dichloromethane (500 mL), washed with 30% ammonium hydroxide (150 mL), sodium thiosulphate (300 mL), brine, dried over anhydrous $Na_2SO_4$ and concentrated. Purification by flash chromatography on silica gel (eluant: dichloromethane/ethanol 95/5) afforded 1.6 g (25%) of the title compound as solid.

$^1$H NMR (300 MHz, DMSO-$d_6$) δ ppm 1.27 (t, J=7.03 Hz, 3 H) 4.00 (s, 3 H) 4.21 (q, J=7.03 Hz, 2 H) 7.44 (d, J=1.76 Hz, 1 H) 7.76 (d, J=1.76 Hz, 1 H) 7.92 (d, J=5.57 Hz, 1 H) 8.40 (d, J=5.57 Hz, 1 H); MS (ESI): 358 [M+H]$^+$.

According to the same method, but employing the suitable starting material, the following compounds were prepared:

5-(2-iodo-pyrimidin-4-yl)-1-(2-fluoro-ethyl)-1H-pyrrole-3-carboxylic acid ethyl ester $^1$H NMR (400 MHz, DMSO-$d_6$) δ ppm 1.29 (t, J=7.07 Hz, 3 H) 4.24 (q, J=7.07 Hz, 2 H) 4.67-4.81 (m, 2 H) 4.81-4.86 (m, 2 H) 7.54 (d, J=1.83 Hz, 1 H) 7.81 (d, J=1.71 Hz, 1 H) 7.97 (d, J=5.49 Hz, 1 H) 8.42 (d, J=5.49 Hz, 1 H); MS (ESI): 390 [M+H]$^+$.

5-(2-iodo-pyrimidin-4-yl)-1-(2,2,2-trifluoro-ethyl)-1H-pyrrole-3-carboxylic acid ethyl ester $^1$H NMR (400 MHz, DMSO-$d_6$) δ ppm 1.29 (t, J=7.07 Hz, 3 H) 4.25 (q, J=7.07 Hz, 2 H) 5.65 (q, J=8.90 Hz, 2 H) 7.63 (d, J=1.83 Hz, 1 H) 7.91 (d, J=1.34 Hz, 1 H) 8.03 (d, J=5.49 Hz, 1 H) 8.46 (d, J=5.37 Hz, 1 H); MS (ESI): 426 [M+H]$^+$.

Step (d'). 5-[2-(5-bromo-2-trifluoromethoxy-phenylamino)-pyrimidin-4-yl]-1-methyl-1H-pyrrole-3-carboxylic acid ethyl ester (A1B1C1M1)

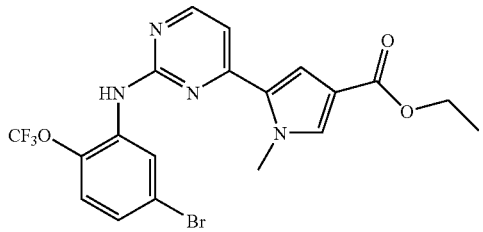

Palladium acetate [Pd(OAc)₂] (0.12 g, 0.55 mmol), (±)-BINAP (0.34 g, 0.55 mmol) and dimethylformamide (60 mL) were charged to a round-bottom flask flushed with argon. The flask was evacuated and backfilled with argon. The mixture was stirred under argon for 30 minutes and added to a mixture of 5-bromo-2-trifluoromethoxy aniline (2.0 g, 5.60 mmol), 5-(2-iodo-pyrimidin-4-yl)-1-methyl-1H-pyrrole-3-carboxylic acid ethyl ester (1.44 g, 5.60 mmol), and potassium carbonate (7.70 g, 55.80 mmol) in dimethylformamide (90 mL). The resulting mixture was stirred at 80° C. for 3 hours under argon. After cooling to room temperature, the reaction mixture was filtered on a pad of celite. The solvent was concentrated, the crude solid was purified by flash chromatography on silica gel (eluant: hexane/ethyl acetate 70/30) to afford 1.41 g (52%) of the title compound as white solid.

$^1$H NMR (400 MHz, DMSO-$d_6$) δ ppm 1.27 (t, J=7.07 Hz, 3 H) 3.92 (s, 3 H) 4.20 (q, J=7.07 Hz, 2 H) 7.29 (d, J=5.37 Hz, 1 H) 7.28 (d, J=1.83 Hz, 1 H) 7.35-7.38 (m, 1 H) 7.38-7.42 (m, 1 H) 7.66 (d, J=1.71 Hz, 1 H) 8.15 (d, J=2.20 Hz, 1 H) 8.40 (d, J=5.37 Hz, 1 H) 9.20 (s, 1 H); MS (ESI): 485 [M+H]⁺.

According to the same method, but employing the suitable starting material, the following compounds were prepared:

5-[2-(5-bromo-2-trifluoromethoxy-phenylamino)-pyrimidin-4-yl]-1-(2-fluoro-ethyl)-1H-pyrrole-3-carboxylic acid ethyl ester (A2B1C1M1)

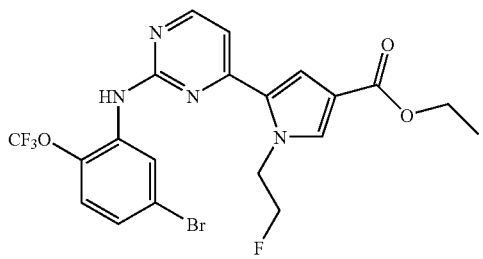

$^1$H NMR (400 MHz, DMSO-$d_6$) δ ppm 1.28 (t, J=7.07 Hz, 3 H) 4.22 (q, J=7.07 Hz, 2 H) 4.35-4.54 (m, 2 H) 4.74-4.87 (m, 2 H) 7.33 (d, J=5.37 Hz, 1 H) 7.38 (d, J=1.83 Hz, 1 H) 7.39-7.43 (m, 1 H) 7.44-7.47 (m, 1 H) 7.68 (d, J=1.59 Hz, 1 H) 8.06 (d, J=2.32 Hz, 1 H) 8.40 (d, J=5.37 Hz, 1 H) 9.21 (s, 1 H); MS (ESI): 517 [M+H]⁺.

5-[2-(5-bromo-2-trifluoromethoxy-phenylamino)-pyrimidin-4-yl]-1-(2,2,2-trifluoro-ethyl)-1H-pyrrole-3-carboxylic acid ethyl ester (A3B1C1M1)

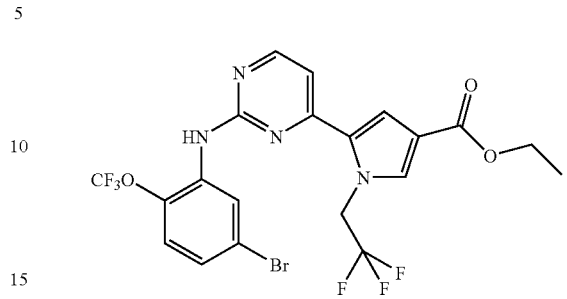

$^1$H NMR (400 MHz, DMSO-$d_6$) δ ppm 1.29 (t, J=7.13 Hz, 3 H) 4.24 (q, J=7.07 Hz, 2 H) 5.63-5.76 (m, 2 H) 7.35 (d, J=5.37 Hz, 1 H) 7.38-7.42 (m, 1 H) 7.42 (d, J=1.83 Hz, 1 H) 7.43-7.47 (m, 1 H) 7.78 (d, J=1.34 Hz, 1 H) 8.10 (d, J=2.32 Hz, 1 H) 8.44 (d, J=5.24 Hz, 1 H) 9.39 (s, 1 H); MS (ESI): 553 [M+H]⁺.

1-methyl-5-{2-[5-(4-methyl-piperazin-1-yl)-2-trifluoromethoxy-phenylamino]-pyrimidin-4-yl}-1H-pyrrole-3-carboxylic acid ethyl ester (A1B1C3M1)

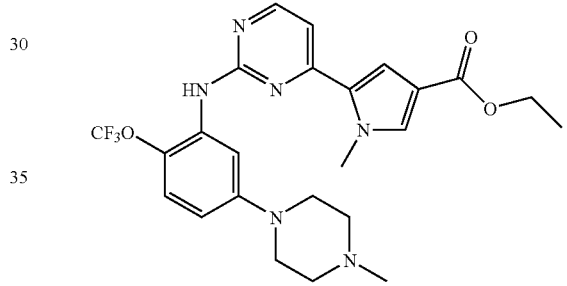

1H NMR (500 MHz, DMSO-$d_6$) δ ppm 1.26 (t, J=7.07 Hz, 3 H) 2.86 (br. S., 3 H) 2.97 (t, J=12.21 Hz, 2 H) 3.09-3.19 (m, 2 H) 3.48-3.54 (m, 2 H) 3.84 (br. S., 2 H) 3.82 (s, 3 H) 4.19 (q, J=7.07 Hz, 2 H) 6.87 (dd, J=9.28, 2.93 Hz, 1 H) 7.19 (d, J=5.37 Hz, 1 H) 7.25 (d, J=1.95 Hz, 1 H) 7.27 (d, J=8.79 Hz, 1 H) 7.32 (d, J=2.44 Hz, 1 H) 7.61 (d, J=1.46 Hz, 1 H) 8.33 (d, J=5.37 Hz, 1 H) 9.01 (s, 1 H) 9.71 (br. S., 1 H); MS (ESI) 505 [M+H]⁺.

5-{2-[5-(4-methyl-piperazin-1-yl)-2-trifluoromethoxy-phenylamino]-pyrimidin-4-yl}-1-(2,2,2-trifluoro-ethyl)-1H-pyrrole-3-carboxylic acid ethyl ester (A3B1C3M1)

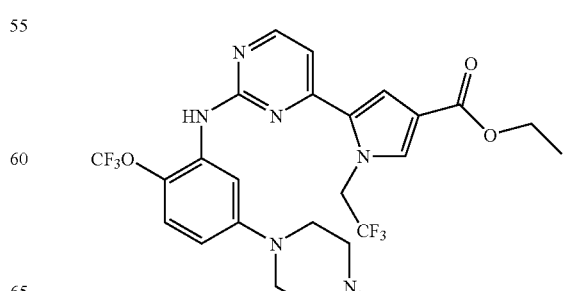

MS (ESI): 505 [M+H]⁺.

31

1-methyl-5-(2-{[4-(4-methylpiperazin-1-yl)-2-(trifluoromethoxy)phenyl]amino}pyrimidin-4-yl)-1H-pyrrole-3-carboxylic acid ethyl ester (A1B1C5M1)

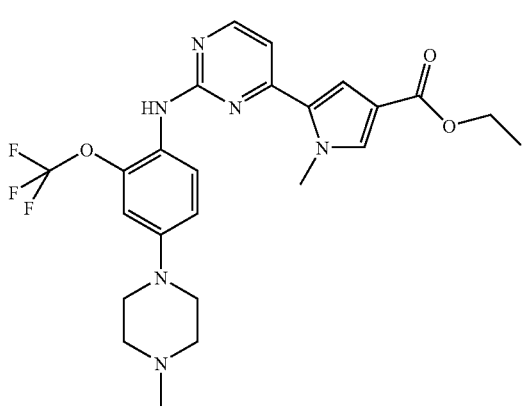 [SMILES: CCOC(=O)c1cc(-c2ccnc(Nc3ccc(N4CCN(C)CC4)cc3OC(F)(F)F)n2)n(C)c1]

1H NMR (400 MHz, DMSO-$d_6$) δ ppm 1.27 (t, J=7.13 Hz, 3 H) 2.24 (s, 3 H) 2.43-2.49 (m, 4 H) 3.12-3.21 (m, 4 H) 3.78 (s, 3 H) 4.20 (q, J=7.07 Hz, 2 H) 6.88 (d, J=1.22 Hz, 1 H) 6.97 (dd, J=8.90, 2.68 Hz, 1 H) 7.11 (d, J=5.24 Hz, 1 H) 7.21 (d, J=1.83 Hz, 1 H) 7.42 (d, J=8.90 Hz, 1 H) 7.59 (d, J=1.71 Hz, 1 H) 8.27 (d, J=5.24 Hz, 1 H) 8.76 (s, 1 H); MS (ESI): 505 [M+H]$^+$.

1-methyl-5-(2-{[2-methoxy-4-(4-methylpiperazin-1-yl)phenyl]amino}pyrimidin-4-yl)-1-methyl-1H-pyrrole-3-carboxylic acid ethyl ester (A1B1C6M1)

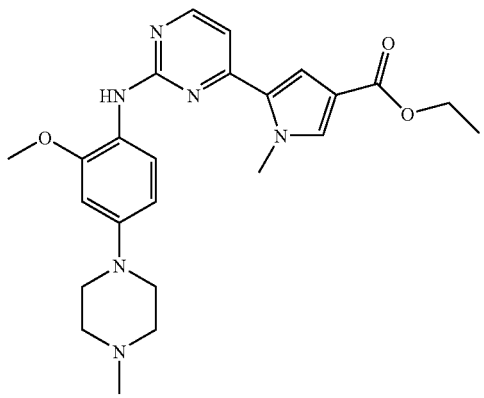 [SMILES: CCOC(=O)c1cc(-c2ccnc(Nc3ccc(N4CCN(C)CC4)cc3OC)n2)n(C)c1]

MS (ESI): 451 [M+H]$^+$.

32

1-methyl-5-[2-({2-methoxy-4-[4-(4-methylpiperazin-1-yl)piperidin-1-yl]phenyl}amino)pyrimidin-4-yl]-1-methyl-1H-pyrrole-3-carboxylic acid ethyl ester (A1B1C7M1)

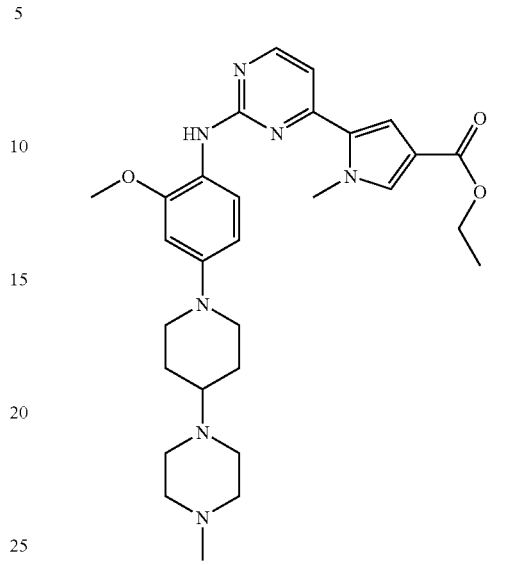

1H NMR (400 MHz, DMSO-$d_6$) δ ppm 1.26 (t, J=7.13 Hz, 5 H) 1.52 (qd, J=11.90, 3.40 Hz, 3 H) 1.85 (d, J=12.07 Hz, 3 H) 2.21 (br. s., 4 H) 2.65 (td, J=11.77, 1.83 Hz, 3 H) 3.69 (dt, J=12.35, 3.22 Hz, 3 H) 3.76 (s, 4 H) 3.85 (s, 3 H) 4.19 (q, J=7.03 Hz, 3 H) 6.48 (dd, J=8.72, 2.50 Hz, 1 H) 6.60 (d, J=2.44 Hz, 1 H) 7.05 (d, J=5.37 Hz, 1 H) 7.18 (d, J=1.83 Hz, 1 H) 7.47 (d, J=8.66 Hz, 1 H) 7.60 (d, J=1.71 Hz, 1 H) 8.05 (s, 1 H) 8.26 (d, J=5.37 Hz, 1 H); MS (ESI): 534 [M+H]$^+$.

Example 2

Conversion (I).

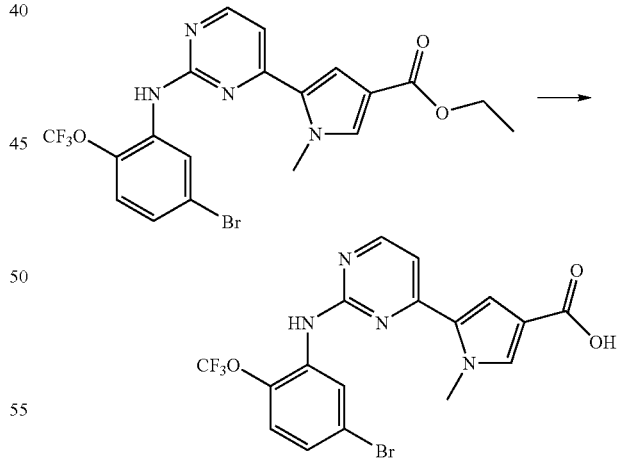

5-[2-(5-Bromo-2-trifluoromethoxy-phenylamino)-pyrimidin-4-yl]-1-methyl-1H-pyrrole-3-carboxylic acid ethyl ester (1.4g, 2.88 mmol) was suspended in anhydrous ethanol (100 mL) and treated with a 2N solution of potassium hydroxide in ethanol (5 mL, 10.00 mmol). The reaction was warmed to 80° C. for 3 hours, the solvent evaporated in vacuo and the residue suspended in water (15 mL) adding acetic acid until pH=4. The suspension was stirred for 1 hour, the precipitated collected by filtration to yield 1.88 g (100%) of the title compound as a pale yellow solid.

33

5-[2-(5-bromo-2-methyl-phenylamino)-pyrimidin-4-yl]-1-methyl-1H-pyrrole-3-carboxylic acid (A1B2C1M1)

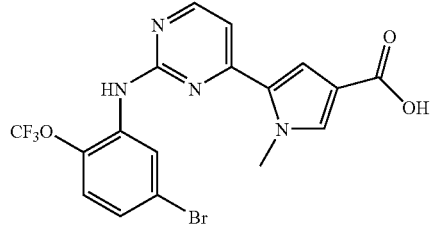

$^1$H NMR (400 MHz, DMSO-d$_6$) δ ppm 3.87 (s, 3 H) 6.78 (br.s., 2 H) 6.93-7.13 (br. s., 1 H) 6.97 (br.s., 2 H) 8.02 (br.s., 2 H); MS (ESI): 457 [M+H]$^+$.

According to the same method, but employing the suitable starting material, the following compounds were prepared:

5-[2-(5-bromo-2-trifluoromethoxy-phenylamino)-pyrimidin-4-yl]-1-(2,2,2-trifluoro-ethyl)-1H-pyrrole-3-carboxylic acid (A3B2C1M1)

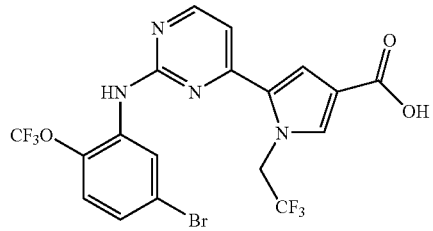

$^1$H NMR (400 MHz, DMSO-d$_6$) δ ppm 5.70 (q, J=9.15 Hz, 2 H) 7.32 (d, J=5.37 Hz, 1 H) 7.38 (d, J=1.83 Hz, 1 H) 7.39-7.42 (m, 1 H) 7.43-7.47 (m, 1 H) 7.71 (d, J=1.34 Hz, 1 H) 8.10 (d, J=2.19 Hz, 1 H) 8.43 (d, J=5.37 Hz, 1 H) 9.37 (s, 1 H) 12.30 (br. s., 1 H); MS (ESI): 525 [M+H]$^+$.

1-methyl-5-{2-[5-(4-methyl-piperazin-1-yl)-2-trifluoromethoxy-phenylamino]-pyrimidin-4-yl}-1H-pyrrole-3-carboxylic acid (A1B2C3M1)

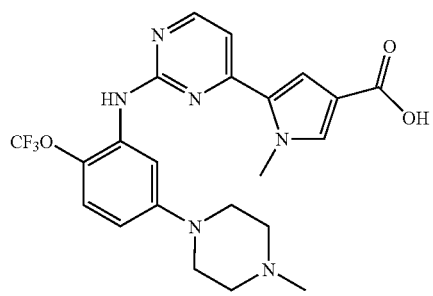

$^1$H NMR (400 MHz, DMSO-d$_6$) δ ppm 2.60-270 (br. s., 2 H) 3.20-3.40 (br. s., 9 H) 3.83 (s, 3 H) 6.85 (dd, J=9.15, 2.93 Hz, 1 H) 7.16 (d, J=5.37 Hz, 1 H) 7.21 (d, J=1.83 Hz, 1 H) 7.24-7.28 (m, 1 H) 7.33 (d, J=2.80 Hz, 1 H) 7.55 (d, J=1.59 Hz, 1 H) 8.34 (d, J=5.37 Hz, 1 H) 8.92 (s, 1 H); MS (ESI): 477 [M+H]$^+$.

34

5-{2-[5-(4-methyl-piperazin-1-yl)-2-trifluoromethoxy-phenylamino]-pyrimidin-4-yl}-1-(2,2,2-trifluoro-ethyl)-1H-pyrrole-3-carboxylic acid (A3B2C3M1)

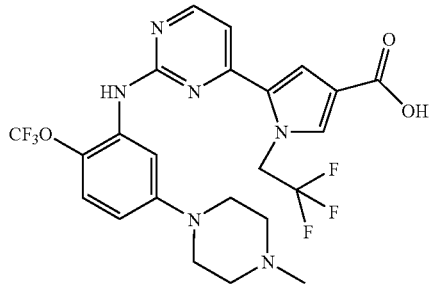

MS (ESI): 544 [M+H]$^+$.

5-{2-[5-(4-Methyl-piperazin-1-yl)-2-trifluoromethoxy-phenylamino]-pyrimidin-4-yl}-1-[2-(tetrahydro-pyran-2-yloxy)-ethyl]-1H-pyrrole-3-carboxylic acid

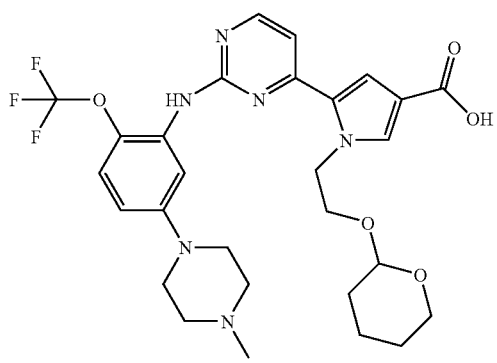 [SMILES: CN1CCN(c2ccc(OC(F)(F)F)c(Nc3nccc(-c4cc(C(=O)O)cn4CCOC4CCCCO4)n3)c2)CC1]

MS (ESI): 591 [M+H]$^+$.

1-methyl-5-(2-{[4-(4-methylpiperazin-1-yl)-2-(trifluoromethoxy)phenyl]amino}pyrimidin-4-yl)-1H-pyrrole-3-carboxylic acid (A1B2C5M1)

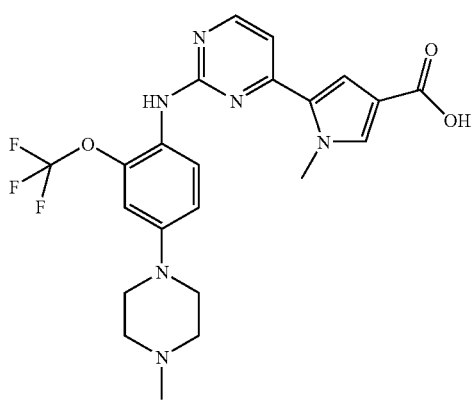 [SMILES: CN1CCN(c2ccc(Nc3nccc(-c4cc(C(=O)O)cn4C)n3)c(OC(F)(F)F)c2)CC1]

MS (ESI): 477 [M+H]$^+$.

5-(2-{[2-methoxy-4-(4-methylpiperazin-1-yl)phenyl]amino}pyrimidin-4-yl)-1-methyl-1H-pyrrole-3-carboxylic acid (A1B2C6M1)

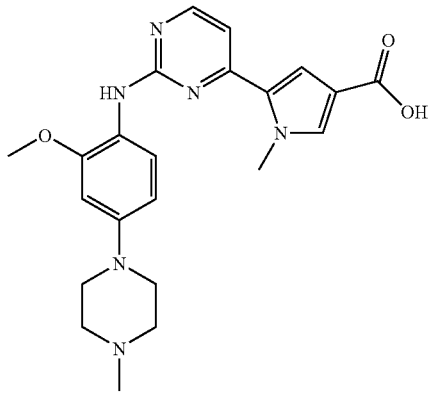 [SMILES: COc1cc(N2CCN(C)CC2)ccc1Nc1nccc(-c2cc(C(=O)O)cn2C)n1]

MS (ESI): 423 [M+H]$^+$.

5-[2-({2-methoxy-4-[4-(4-methylpiperazin-1-yl)piperidin-1-yl]phenyl}amino)pyrimidin-4-yl]-1-methyl-1H-pyrrole-3-carboxylic acid (A1B2C7M1)

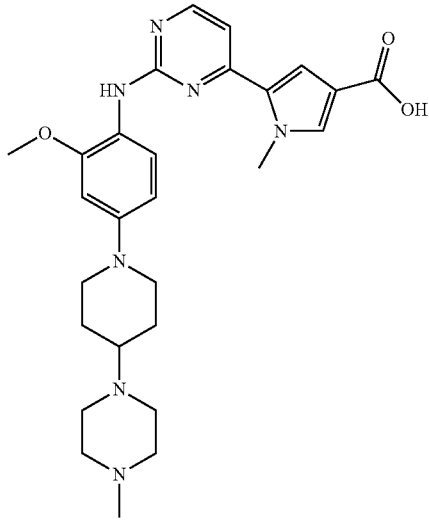 [SMILES: COc1cc(N2CCC(N3CCN(C)CC3)CC2)ccc1Nc1nccc(-c2cc(C(=O)O)cn2C)n1]

MS (ESI): 506 [M+H]$^+$.

Example 3

Conversion (I).

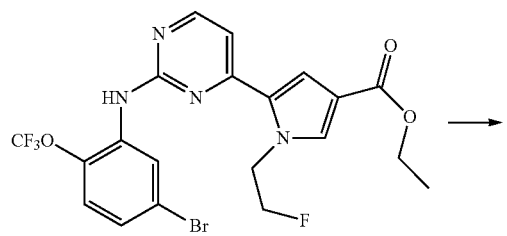

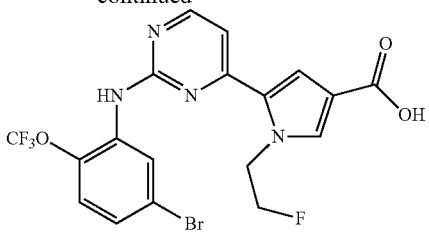

To a solution of 5-[2-(5-bromo-2-trifluoromethoxy-phenylamino)-pyrimidin-4-yl]-1-(2-fluoro-ethyl)-1H-pyrrole-3-carboxylic acid ethyl ester (340 mg, 0.66 mmol) in acetonitril (10 mL), 36% HCl (5 mL) were added. The reaction was heated to 70° C. and stirred for five days. The solvent was evaporated under vacuum and the residue suspended in water (20 mL) and stirred for 1 hour. The white solid was collected by filtration and dried in the oven under vacuum at 30° C. to yield 345 mg (98%) of the title compound.

5-[2-(5-bromo-2-trifluoromethoxy-phenylamino)-pyrimidin-4-yl]-1-(2-fluoro-ethyl)-1H-pyrrole-3-carboxylic acid hydrochloride (A2B2C1M1)

$^1$H NMR (400 MHz, DMSO-d$_6$) δ ppm 4.35-4.53 (m, 2 H) 4.72-4.85 (m, 2 H) 7.31 (d, J=5.49 Hz, 1 H) 7.35 (d, J=1.83 Hz, 1 H) 7.39-7.43 (m, 1 H) 7.44-7.48 (m, 1 H) 7.62 (d, J=1.34 Hz, 1 H) 8.06 (d, J=2.32 Hz, 1 H) 8.39 (d, J=5.37 Hz, 1 H) 9.23 (s, 1 H); MS (ESI): 489 [M+H]$^+$.

Example 4

Conversion (III).

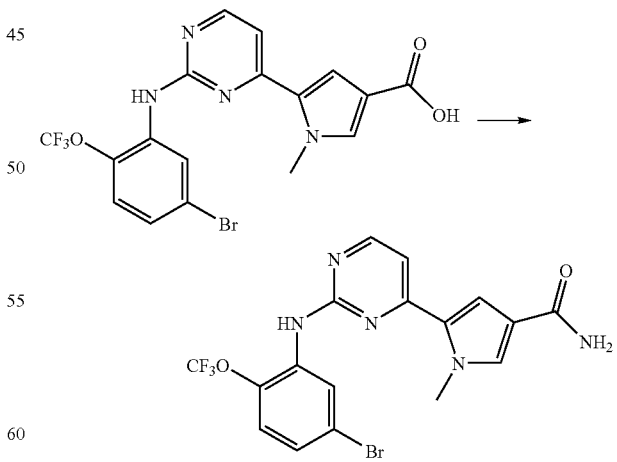

A suspension of sodium 5-[2-(5-bromo-2-methyl-phenylamino)-pyrimidin-4-yl]-1-methyl-1H-pyrrole-3-carboxylic acid (1.80 g, 3.78 mmol) in 1:1 mixture of anhydrous dimethylformamide dichloromethane (100 mL) was treated with N-ethyl-N',N'-diisopropyl carbodiimide hydrochloride (EDCI) (1.82 g, 5.67 mmol), with ammonium 1H-1,2,3-benzotriazol-1-ate (0.86 g, 5.67 mmol) and with triethylamine mmol). The reaction was stirred at room temperature overnight. The reaction was diluted with water and the resulting precipitate was collected by filtration to afford 1.4 g (82%) of the title compound as a yellow powder.

5-[2-(5-bromo-2-trifluoromethoxy-phenylamino)-pyrimidin-4-yl]-1-methyl-1H-pyrrole-3-carboxylic acid amide (A1B3C1M1)

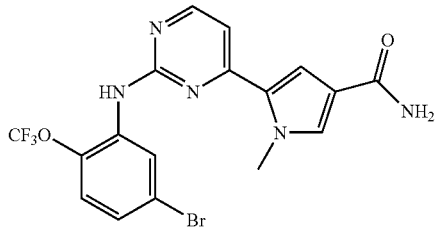

$^1$H NMR (400 MHz, DMSO-d$_6$) δ ppm 3.91 (s, 3 H) 6.85 (br. s., 1 H) 7.12 (d, J=5.37 Hz, 1 H) 7.31 (d, J=1.95 Hz, 1 H) 7.35-7.42 (m, 3 H) 7.49-7.51 (m, 1 H) 8.17 (d, J=2.07 Hz, 1 H) 8.41 (d, J=5.37 Hz, 1 H) 9.17 (s, 1 H); MS (ESI): 456 [M+H]$^+$.

According to the same method, but employing the suitable starting material, the following compounds were prepared:

5-[2-(5-bromo-2-trifluoromethoxy-phenylamino)-pyrimidin-4-yl]-1-(2-fluoro-ethyl)-1H-pyrrole-3-carboxylic acid amide (A2B3C1M1)

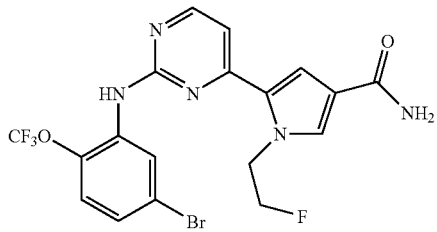

$^1$H NMR (400 MHz, DMSO-d$_6$) δ ppm 4.36-4.52 (m, 2 H) 4.69-4.80 (m, 2 H) 6.89 (br. s., 1 H) 7.14 (d, J=5.37 Hz, 1 H) 7.39-7.43 (m, 1 H) 7.39-7.40 (m, 1 H) 7.43-7.47 (m, 1 H) 7.55 (d, J=1.59 Hz, 1 H) 8.06 (d, J=2.19 Hz, 1 H) 8.40 (d, J=5.37 Hz, 1 H) 9.18 (s, 1 H); MS (ESI): 488 [M+H]$^+$.

5-[2-(5-bromo-2-trifluoromethoxy-phenylamino)-pyrimidin-4-yl]-1-(2,2,2-trifluoro-ethyl)-1H-pyrrole-3-carboxylic acid amide (A3B3C1M1)

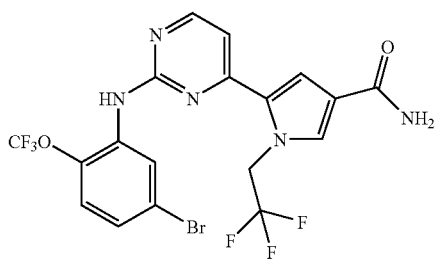

$^1$H NMR (400 MHz, DMSO-d$_6$) δ ppm 5.66 (q, J=9.23 Hz, 2 H) 7.01 (br. s., 1 H) 7.14 (d, J=5.37 Hz, 1 H) 7.37-7.42 (m, 1 H) 7.43-7.44 (m, 1 H) 7.44-7.47 (m, 1 H) 7.61 (s, 1 H) 8.09 (d, J=2.32 Hz, 1 H) 8.43 (d, J=5.37 Hz, 1 H) 9.36 (s, 1 H); MS (ESI): 524 [M+H]$^+$.

5-{2-[5-(4-Methyl-piperazin-1-yl)-2-trifluoromethoxy-phenylamino]-pyrimidin-4-yl}-1-[2-(tetrahydro-pyran-2-yloxy)-ethyl]-1H-pyrrole-3-carboxylic acid amide

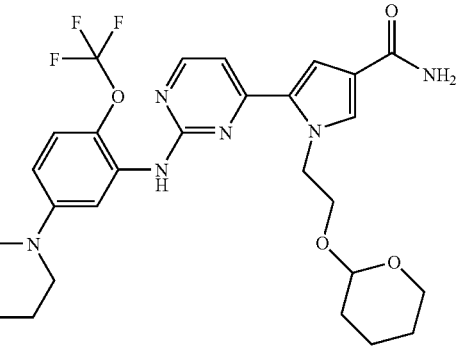

MS (ESI): 590 [M+H]$^+$.

1-methyl-5-(2-{[4-(4-methylpiperazin-1-yl)-2-(trifluoromethoxy)phenyl]amino}pyrimidin-4-yl)-1H-pyrrole-3-carboxamide (A1B3C5M1)

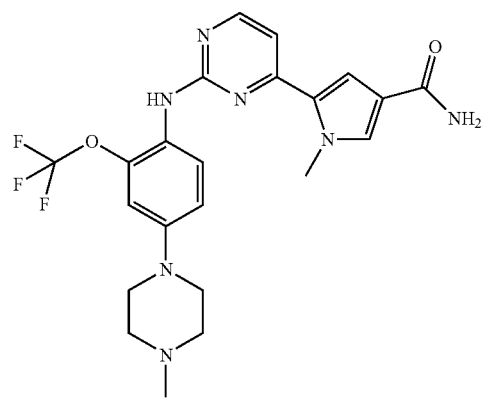 [SMILES: CN1CCN(c2ccc(Nc3nccc(-c4cc(C(N)=O)cn4C)n3)c(OC(F)(F)F)c2)CC1]

$^1$H NMR (400 MHz, DMSO-d$_6$) δ ppm 2.25 (s, 3 H) 2.48 (br. s., 4 H) 3.13-3.19 (m, 4 H) 3.76 (s, 3 H) 6.81 (br. s., 1 H) 6.87 (d, J=1.10 Hz, 1 H) 6.94 (d, J=5.37 Hz, 1 H) 6.95-6.99 (m, 1 H) 7.23 (d, J=1.83 Hz, 1 H) 7.36 (d, J=4.02 Hz, 1 H) 7.41-7.46 (m, 2 H) 8.27 (d, J=5.37 Hz, 1 H) 8.72 (s, 1 H)); MS (ESI): 476 [M+H]$^+$.

5-(2-{[2-methoxy-4-(4-methylpiperazin-1-yl)phenyl]amino}pyrimidin-4-yl)-1-methyl-1H-pyrrole-3-carboxamide (A1B3C6M1)

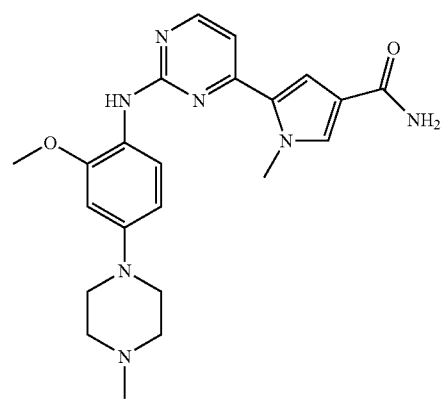 [SMILES: COc1cc(N2CCN(C)CC2)ccc1Nc1nccc(-c2cc(C(N)=O)cn2C)n1]

$^1$H NMR (401 MHz, DMSO-$d_6$) δ ppm 2.23 (s, 3 H) 2.46 (t, J=4.90 Hz, 4 H) 3.12 (t, J=4.90 Hz, 4 H) 3.78 (s, 3 H) 3.84 (s, 3 H) 6.48 (dd, J=8.66, 2.56 Hz, 1 H) 6.61 (d, J=2.44 Hz, 1 H) 6.81 (br. s., 1 H) 6.91 (d, J=5.24 Hz, 1 H) 7.21 (d, J=1.95 Hz, 1 H) 7.44 (d, J=1.71 Hz, 1 H) 7.54 (d, J=8.66 Hz, 1 H) 8.00 (s, 1 H) 8.26 (d, J=5.24 Hz, 1 H); MS (ESI): 422 [M+H]$^+$.

5-[2-({2-methoxy-4-[4-(4-methylpiperazin-1-yl)piperidin-1-yl]phenyl}amino)pyrimidin-4-yl]-1-methyl-1H-pyrrole-3-carboxamide (A1B3C7M1)

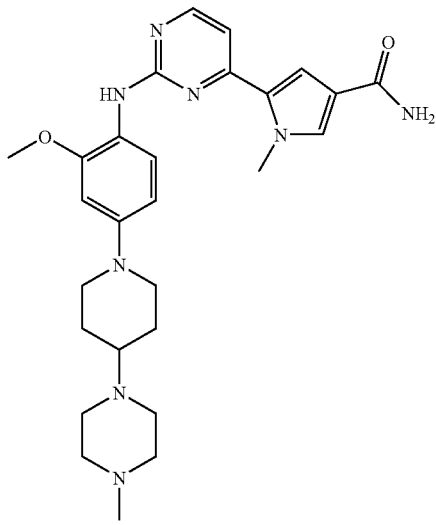 [SMILES: COc1cc(N2CCC(N3CCN(C)CC3)CC2)ccc1Nc1nccc(-c2cc(C(N)=O)cn2C)n1]

$^1$H NMR (400 MHz, DMSO-$d_6$) δ ppm 1.51 (qd, J=11.91, 3.66 Hz, 2 H) 1.84 (d, J=13.05 Hz, 2 H) 2.15 (s, 3 H) 2.30 (tt, J=11.30, 3.70 Hz, 1 H) 2.64 (td, J=12.53, 1.77 Hz, 2 H) 3.69 (d, J=12.32 Hz, 2 H) 3.77 (s, 3 H) 3.84 (s, 3 H) 6.48 (dd, J=8.78, 2.56 Hz, 1 H) 6.60 (d, J=2.44 Hz, 1 H) 6.81 (br. s., 1 H) 6.90 (d, J=5.24 Hz, 1 H) 7.21 (d, J=1.95 Hz, 1 H) 7.37 (br. s., 1 H) 7.43 (d, J=1.83 Hz, 1 H) 7.51 (d, J=8.66 Hz, 1 H) 7.99 (s, 1 H) 8.26 (d, J=5.24 Hz, 1 H); MS (ESI): 505 [M+H]$^+$.

Example 5

Conversion (IV).

4-{3-[4-(4-carbamoyl-1-methyl-1H-pyrrol-2-yl)-pyrimidin-2-ylamino]-4-trifluoromethoxy-phenyl}-piperazine-1-carboxylic acid tert-butyl ester

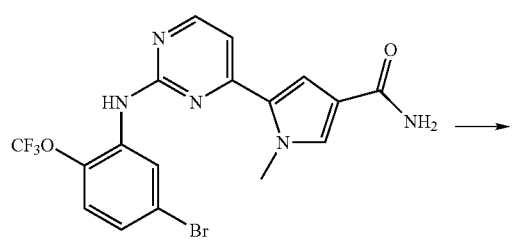

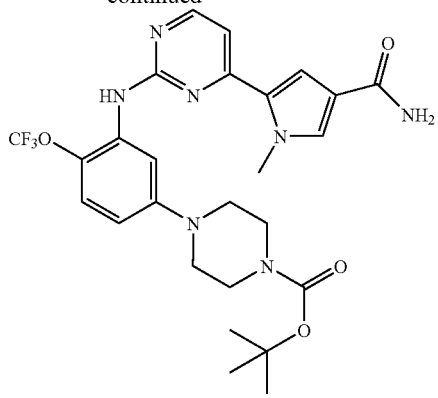

Tris(dibenzilideneacetone)dipalladium, Pd$_2$(dba)$_3$, (30 mg, 0.03 mmol), 2-dicyclohexylphosphino-2'-(N,N-dimethylamino)-biphenyl (7 mg, 0.01 mmol), 5-[2-(5-Bromo-2-trifluoromethoxy-phenylamino)-pyrimidin-4-yl]-1-methyl-1H-pyrrole-3-carboxylic acid amide (300 mg, 0.66 mmol) in THF (4.5 mL) were charged in a round-bottom flask flushed with argon. The flask was evacuated and backfilled with argon.

Lithium bis(trimethylsilyl)amide solution (1M in THF, 4.0 mL) and piperazine-1-carboxylic acid tert-butyl ester (247 mg, 1.33 mmol) were added and the reaction mixture refluxed for 5 h. The reaction mixture was then allowed to cool to room temperature and concentrated. The crude solid was purified by flash chromatography on silica gel (eluant: DCM/EtOH 95/5) to afford 185 mg (50% yield) of the title compound.

$^1$H NMR (400 MHz, DMSO-$d_6$) δ ppm 1.43 (s, 9 H) 3.09-3.15 (m, 4 H) 3.43-3.48 (m, 4 H) 3.81 (s, 3 H) 6.81 (dd, J=9.08, 2.99 Hz, 1 H) 6.83 (br. s., 1 H) 7.02 (d, J=5.37 Hz, 1 H) 7.20-7.25 (m, 1 H) 7.26 (d, J=1.95 Hz, 1 H) 7.30 (d, J=2.93 Hz, 1 H) 7.39 (br. s., 1 H) 7.44 (d, J=1.83 Hz, 1 H) 8.33 (d, J=5.24 Hz, 1 H) 8.85 (s, 1 H); MS (ESI): 562 [M+H]$^+$.

According to the same method, but employing the suitable starting material, the following compounds were prepared:

1-methyl-5-{2-[5-(4-methyl-piperazin-1-yl)-2-trifluoromethoxy-phenylamino]-pyrimidin-4-yl}-1H-pyrrole-3-carboxylic acid amide (A1B3C3M1)

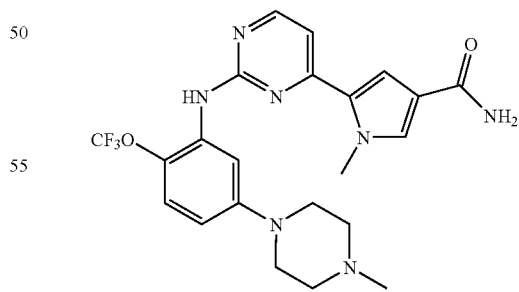

$^1$H NMR (400 MHz, DMSO-$d_6$) δ ppm 2.22 (s, 3 H) 2.41-2.48 (m, 4 H) 3.08-3.19 (m, 4 H) 3.81 (s, 3 H) 6.79 (dd, J=9.21, 2.99 Hz, 1 H) 6.82 (br. s., 1 H) 7.01 (d, J=5.37 Hz, 1 H) 7.17-7.23 (m, 1 H) 7.25-7.28 (m, 2 H) 7.37 (br. s., 1 H) 7.45 (d, J=1.83 Hz, 1 H) 8.33 (d, J=5.24 Hz, 1 H) 8.81 (s, 1 H); MS (ESI): 476 [M+H]$^+$.

5-{2-[5-(4-methyl-piperazin-1-yl)-2-trifluoromethoxy-phenylamino]-pyrimidin-4-yl}-1-(2,2,2-trifluoro-ethyl)-1H-pyrrole-3-carboxylic acid amide (A3B3C3M1)

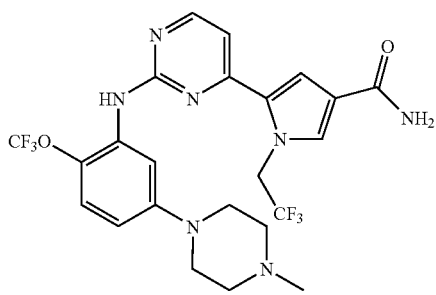

$^1$H NMR (400 MHz, DMSO-d$_6$) δ ppm 2.28 (br. s., 3 H) 2.51 (br. s., 4 H) 3.17 (br. s., 4 H) 5.48-5.67 (m, 2 H) 6.83 (dd, J=9.08, 2.99 Hz, 1 H) 6.99 (br. s., 1 H) 7.03 (d, J=5.24 Hz, 1 H) 7.17 (d, J=2.68 Hz, 1 H) 7.22 (dd, J=9.08, 1.16 Hz, 1 H) 7.37 (d, J=1.95 Hz, 1 H) 7.53 (br. s., 1 H) 7.56 (d, J=1.22 Hz, 1 H) 8.36 (d, J=5.37 Hz, 1 H) 9.06 (s, 1 H); MS (ESI): 544 [M+H]$^+$.

1-methyl-5-[2-(5-piperazin-1-yl-2-trifluoromethoxy-phenylamino)-pyrimidin-4-yl]-1H-pyrrole-3-carboxylic acid amide (A1B3C2 M1)

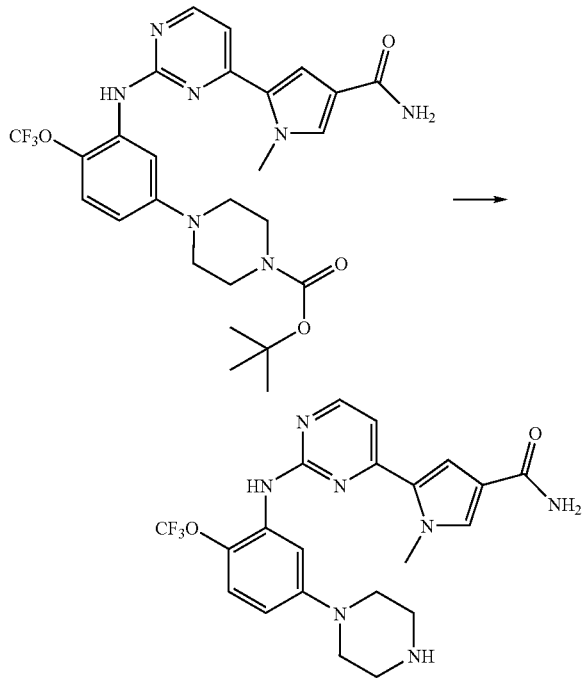

To a solution of 4-{3-[4-(4-carbamoyl-1-methyl-1H-pyrrol-2-yl)-pyrimidin-2-ylamino]-4-trifluoromethoxy-phenyl}-piperazine-1-carboxylic acid tert-butyl ester (176 mg, 0.314 mmol) in dioxane (3 mL), HCl in dioxane solution (4N, 4 mL) were added. The reaction was stirred at room temperature for 6 hours and the precipitate collected by filtration. The precipitate was dissolved in HCl water solution (0.1N, 30 mL) and washed with dichloromethane (50 mL). The aqueous layers were collected and the title compound precipitated by addition of sodium bicarbonate. The aqueous phase was eliminated by filtration, the solid washed with water (10 mL) and dried under vacuo at 30° C. to yield 96 mg (66%) of the title compound as an hazelnut powder.

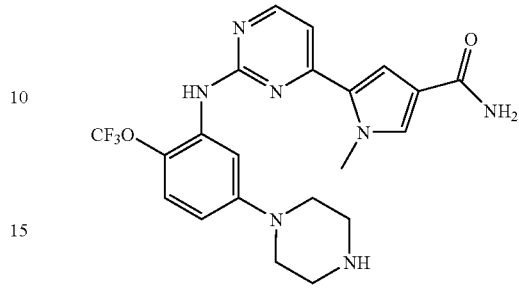

$^1$H NMR (400 MHz, DMSO-d$_6$) δ ppm 2.79-2.84 (m, 4 H) 3.04 (qq, 4 H) 3.81 (s, 3 H) 6.77 (dd, J=9.08, 2.99 Hz, 1 H) 6.83 (br. s., 1 H) 7.01 (d, J=5.24 Hz, 1 H) 7.16-7.23 (m, 1 H) 7.23-7.27 (m, 2 H) 7.37 (br.s., 1 H) 7.45 (d, J=1.71 Hz, 1 H) 8.33 (d, J=5.37 Hz, 1 H) 8.80 (s, 1 H); MS (ESI): 462 [M+H]$^+$.

Example 6

2-trifluoromethoxy-5-(4-methyl-piperazin-1-yl)-phenylamine trihydrochloride salt and 1-(3-iodo-4-trifluoromethoxy-phenyl)-4-methyl-piperazine Step 1: N-(5-bromo-2-trifluoromethoxy-phenyl)-acetamide

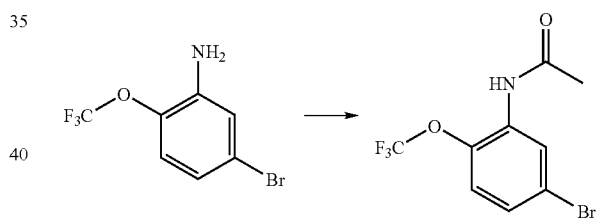

To a solution of 2-trifluoromethoxy-5-bromo-phenylamine (5.12 g, 20 mmol) in EtOH (50 mL) at 0° C. was added a solution of acetic anhydride (4.7 mL, 50 mmol) in EtOH (10 mL). The mixture was stirred at room temperature overnight. The solvent was evaporated to dryness and the solid was tritured with diethyl ether and filtered to give 5.64 g (95% yield) of N-(5-bromo-2-trifluoromethoxy-phenyl)-acetamide.

$^1$H NMR (400 MHz, DMSO-d$_6$) δ ppm: 2.11 (s, 3 H) 7.39 (m, 2 H) 8.21 (s, 1 H) 9.87 (s, 1 H); MS (ESI): 257 [M+H]$^+$.

Step 2: N-[2-trifluoromethoxy-5-(4-methyl-piperazin-1-yl)-phenyl]-acetamide

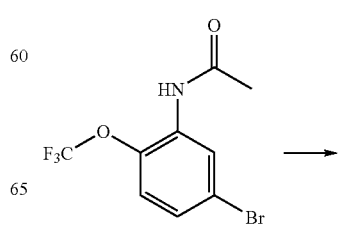

-continued

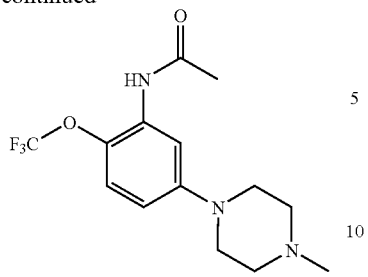

Pd₂(dba)₃ (157 mg, 0.17 mmol), 2-dicyclohexylphosphino-2'-(N,N-dimethylamino)-biphenyl (134.7 mg, 0.34 mmol), N-(5-bromo-2-trifluoromethoxy-phenyl)-acetamide (5.05 g, 17 mmol)) were charged in a round-bottom flask flushed with argon. The flask was evacuated and backfilled with argon. Lithium bis(trimethylsilyl)amide solution (1M in THF, 37.6 mL) and N-methylpiperazine (2.3 mL, 20.5 mmol) were added and the reaction mixture refluxed for 3 h. The reaction mixture was then allowed to cool to room temperature and concentrated. The crude solid was purified by flash chromatography on silica gel (eluant: DCM/EtOH 90/10) to afford 4.78 g (88% yield) of the N-[2-trifluoromethoxy-5-(4-methyl-piperazin-1-yl)-phenyl]-acetamide.

¹H NMR (400 MHz, DMSO-d₆) δ ppm: 2.06 (s, 3 H) 2.22 (s, 3 H) 2.45 (m, 4 H) 3.11 (m, 4 H) 6.75 (dd, J=9.15 and 3.05 Hz, 1 H) 7.17 (dd, J=9.15 and 1.46 Hz, 1 H) 7.41 (bs, 1 H) 9.54 (s, 1 H); MS (ESI): 299 [M+H]⁺.

Step 3: 2-trifluoromethoxy-5-(4-methyl-piperazin-1-yl)-phenylamine trihydrochloride salt

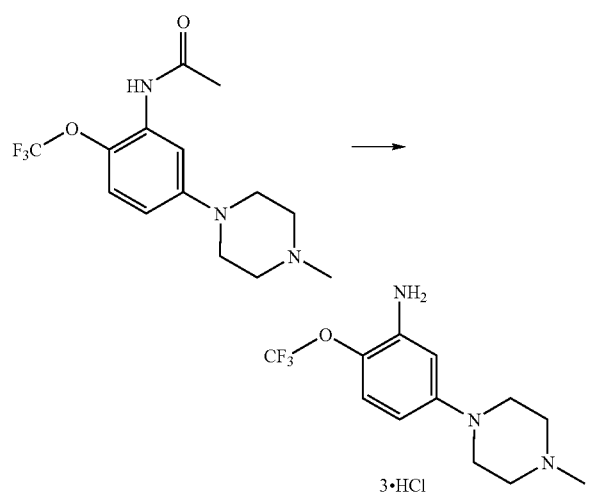

A solution of N-[2-trifluoromethoxy-5-(4-methyl-piperazin-1-yl)-phenyl]-acetamide (4.75 g, 15 mmol) in EtOH (100 mL) was treated with HCl 37% (35 mL). After 1 h under reflux the mixture was concentrated and tritured with hexane to give in quantitative yield, 5.74 g of 2-trifluoromethoxy-5-(4-methyl-piperazin-1-yl)-phenylamine trihydrochloride salt.

¹H NMR (400 MHz, DMSO-d₆) δ ppm: 2.82 (d, J=4.76 Hz 3 H) 3.1 (m, 4 H) 3.48 (m, 4 H) 6.24 (dd, J=8.90 and 2.93 Hz, 1 H) 6.40 (d, J=2.93 Hz, 1 H) 6.98 (dd, J=8.90 and 1.34 Hz, 1 H) 10.31 (bs, 1 H); MS (ESI): 318 [M+H]⁺.

According to the same method, but employing the suitable starting material, the following compound was prepared:

2-methoxy-5-(4-methyl-piperazin-1-yl)-phenylamine

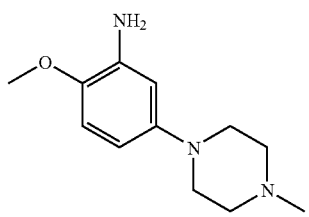

1H NMR (400 MHz, DMSO-d₆) δ ppm 2.21 (s, 3 H) 2.40-2.46 (m, 4 H) 2.92-2.96 (m, 4 H) 3.65-3.69 (m, 3 H) 4.55 (s, 2 H) 6.09 (dd, J=8.66, 2.93 Hz, 1 H) 6.31 (d, J=2.80 Hz, 1 H) 6.64 (d, J=8.66 Hz, 1 H); MS (ESI): 222 [M+H]⁺.

Step 4: 1-(3-iodo-4-trifluoromethoxy-phenyl)-4-methyl-piperazine

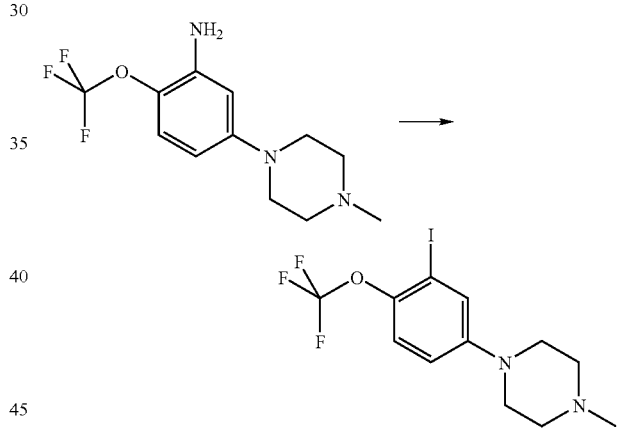

To a solution of 2-trifluoromethoxy-5-(4-methyl-piperazin-1-yl)-phenylamine (5.0 g, 0.018 mol), sodium nitrite (5.1 g, 0.0734 mol) in dimethyl sulfoxide (180 mL) a solution of 57% hydroiodic acid (9.6. mL, 0.0427 mol) in dimethyl sulfoxide were added dropwise at room temperature in 20 minutes. The reaction was stirred for 5 hours at 35° C., then cooled in a ice bath and sodium bicarbonate in small portion was added until basic pH. The aqueous layer was extracted with dichoromethane (3×500 mL), the organic phases washed with 10% solution of sodium bisulphite (2×500 mL) then water (1×300 mL). The organic phase was dried over anhydrous Na₂SO₄, the solvent evaporated under vacuum to yield the intermediate (2.4 g, 34%) as a orange solid which was used as such in the next step.

¹H NMR (400 MHz, DMSO-d₆) δ ppm: 2.22 (s, 3 H) 2.38-2.46 (m, 4 H) 3.13-3.20 (m, 4 H) 7.02 (dd, J=9.05, 2.90 Hz, 1 H) 7.22 (d, J=9.05 Hz, 1 H) 7.38 (d, J=2.90, 1 H); MS (ESI): 387 [M+H]⁺.

According to the same method, but employing the suitable starting material, the following compound was prepared:

1-(3-iodo-4-methoxy-phenyl)-4-methyl-piperazine

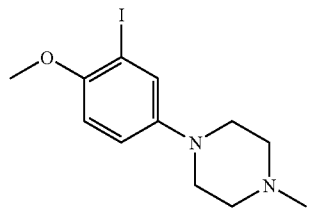

1H NMR (400 MHz, DMSO-d$_6$) δ ppm 2.22 (s, 3 H) 2.44 (d, J=9.39 Hz, 4 H) 2.99-3.04 (m, 4 H) 3.74 (s, 3 H) 6.86-6.91 (m, 1 H) 6.93-6.98 (m, 1 H) 7.30 (d, J=2.80 Hz, 1 H); MS (ESI): 333 [M+H]$^+$.

Example 7

Step (c). 1-methyl-2-{2-[5-(4-methyl-piperazin-1-yl)-2-trifluoromethoxy-phenylamino]-pyrimidin-4-yl}-4-oxo-1,4,6,7-tetrahydro-pyrrolo[3,2-c]pyridine-5-carboxylic acid tert-butyl ester

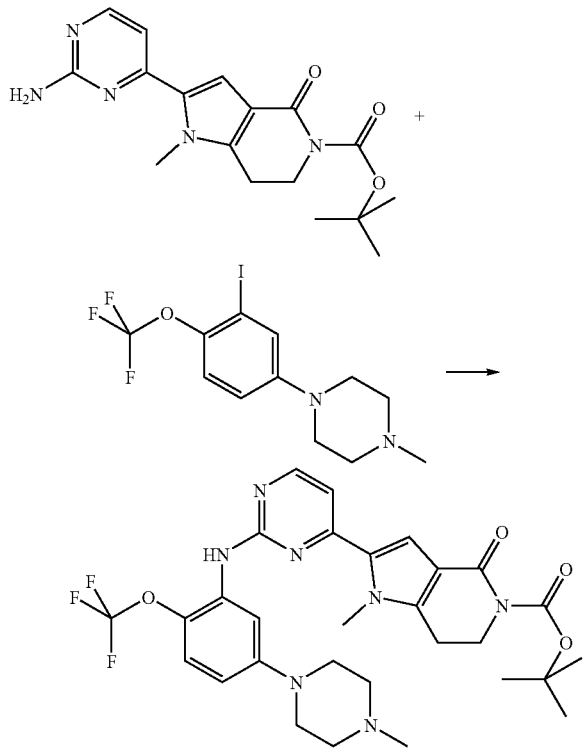

Tris(dibenzilideneacetone)dipalladium, Pd$_2$(dba)$_3$, (165 mg, 0.18 mmol), 4,5-bis(diphenylphosphino)-9,9-dimethylxanthene (228 mg, 0.39 mmol), 1-(3-iodo-4-trifluoromethoxy-phenyl)-4-methyl-piperazine prepared as reported in Example 6 (1.53 g, 3.98 mmol), 2-(2-Amino-pyrimidin-4-yl)-1-methyl-4-oxo-1,4,6,7-tetrahydro-pyrrolo[3,2-c]pyridine-5-carboxylic acid tert-butyl ester prepared as reported in Example 9 (1.36 g, 3.98 mmol), cesium carbonate (2.58 g, 7.90 mmol) in dioxane (30 mL) were charged in a round-bottom flask flushed with argon.

The reaction mixture was refluxed for 5 h then allowed to cool to room temperature and concentrated. The crude solid was purified by flash chromatography on silica gel (eluant: DCM/EtOH 95/5) to afford 2.03 g (85% yield) of the title compound.

$^1$H NMR (400 MHz, DMSO-d$_6$) δ ppm 1.47 (s, 9 H) 2.23 (s, 3 H) 2.43-2.48 (m, 4 H) 2.93 (t, J=6.34 Hz, 2 H) 3.12-3.17 (m, 4 H) 3.73 (s, 3 H) 3.96 (t, J=6.28 Hz, 2 H) 6.80 (dd, J=9.15, 3.05 Hz, 1 H) 7.15 (d, J=5.37 Hz, 1 H) 7.20 (d, J=9.02 Hz, 1 H) 7.20 (s, 1 H) 7.24 (d, J=2.93 Hz, 1 H) 8.33 (d, J=5.37 Hz, 1 H) 8.88 (s, 1 H); MS (ESI): 602 [M+H]$^+$.

According to the same method, but employing the suitable starting material, the following compounds were prepared:

1-(2-hydroxy-ethyl)-2-{2-[5-(4-methyl-piperazin-1-yl)-2-trifluoromethoxy-phenylamino]-pyrimidin-4-yl}-4-oxo-1,4,6,7-tetrahydro-pyrrolo[3,2-c]pyridine-5-carboxylic acid tert-butyl ester

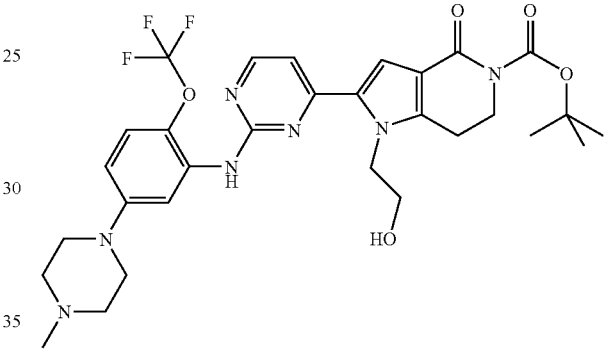

MS (ESI): 632 [M+H]$^+$.

2-{2-[5-(4-methyl-piperazin-1-yl)-2-trifluoromethoxy-phenylamino]-pyrimidin-4-yl}-4-oxo-1-[2-(tetrahydro-pyran-2-yloxy)-ethyl]-1,4,6,7-tetrahydro-pyrrolo[3,2-c]pyridine-5-carboxylic acid tert-butyl ester

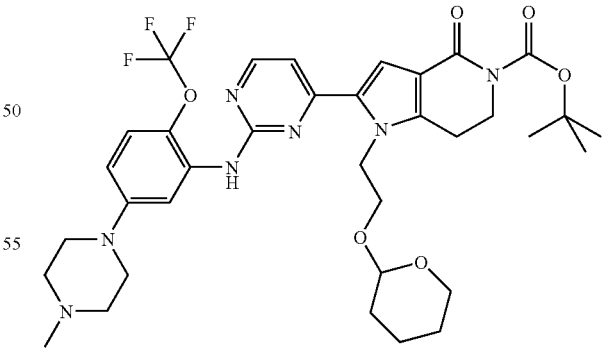

$^1$H NMR (401 MHz, DMSO-d$_6$) δ ppm 1.47 (s, 9 H) 2.23 (s, 3 H) 2.42-2.49 (m, 4 H) 2.98 (t, J=6.34 Hz, 2 H) 3.13-3.18 (m, 4 H) 3.91-3.97 (m, 2 H) 4.29 (t, J=2.93 Hz, 1 H) 4.49 (br. s., 2 H) 6.83 (dd, J=9.14, 3.05 Hz, 1 H) 7.13 (d, J=2.80 Hz, 1 H) 7.18 (d, J=5.36 Hz, 1 H) 7.22 (dd, J=8.96, 1.28 Hz, 1 H) 7.29 (s, 1 H) 8.31 (d, J=5.24 Hz, 1 H) 8.88 (s, 1 H); MS (ESI): 716 [M+H]$^+$.

2-{2-[2-methoxy-5-(4-methyl-piperazin-1-yl)-phenylamino]pyrimidin-4-yl}-4-oxo-1-[2-(tetrahydro-pyran-2-yloxy)-ethyl]-1,4,6,7-tetrahydro-pyrrolo[3,2-c]pyridine-5-carboxylic acid tert-butyl ester

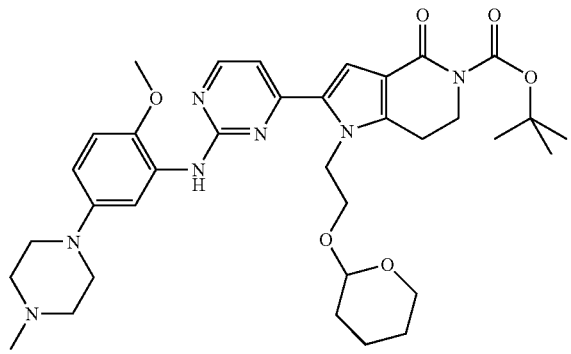 [SMILES: COc1ccc(N2CCN(C)CC2)cc1Nc1nccc(-c2cc3c(n2CCOC2CCCCO2)CCN(C(=O)OC(C)(C)C)C3=O)n1]

MS (ESI): 662 [M+H]$^+$.

According to the same method, but employing the suitable starting material, the following compound was prepared:

5-{2-[5-(4-Methyl-piperazin-1-yl)-2-trifluoromethoxy-phenylamino]-pyrimidin-4-yl}-1-[2-(tetrahydro-pyran-2-yloxy)-ethyl]-1H-pyrrole-3-carboxylic acid ethyl ester

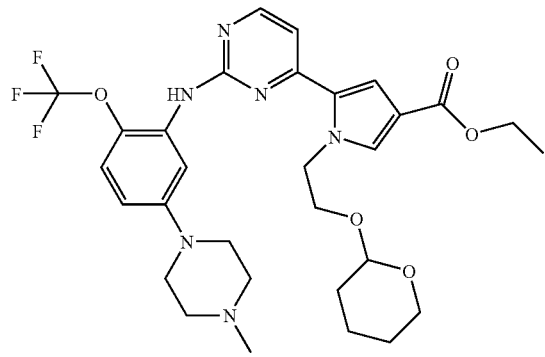 [SMILES: CCOC(=O)c1cc(-c2ccnc(Nc3cc(N4CCN(C)CC4)ccc3OC(F)(F)F)n2)n(CCOC2CCCCO2)c1]

$^1$H NMR (500 MHz, DMSO-d$_6$) δ ppm 1.25 (t, J=7.14 Hz, 3 H) 2.20 (s, 3 H) 2.40-2.45 (m, 4 H) 3.11-3.15 (m, 4 H) 4.15-4.23 (m, 2 H) 4.32 (t, J=3.11 Hz, 1 H) 4.48-4.62 (m, 2 H) 6.81 (dd, J=9.09, 2.99 Hz, 1 H) 7.15 (d, J=2.81 Hz, 1 H) 7.17 (d, J=5.37 Hz, 1 H) 7.19-7.22 (m, 1 H) 7.26 (d, J=1.71 Hz, 1 H) 7.59 (d, J=1.83 Hz, 1 H) 8.31 (d, J=5.25 Hz, 1 H) 8.89 (s, 1 H); MS (ESI): 619 [M+H]$^+$.

Step (d). 1-methyl-2-{2-[5-(4-methyl-piperazin-1-yl)-2-trifluoromethoxy-phenylamino]-pyrimidin-4-yl}-1,5,6,7-tetrahydro-pyrrolo[3,2-c]pyridin-4-one hydrochloride (A1C3M2)

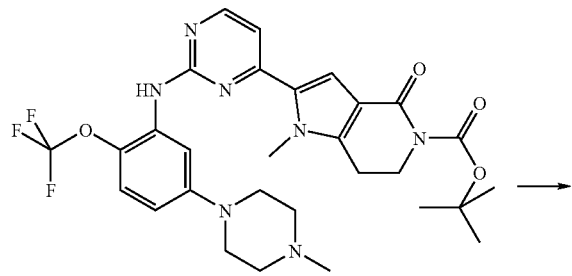

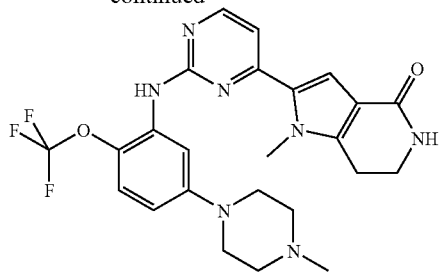

To a solution of methyl-2-{2-[5-(4-methyl-piperazin-1-yl)-2-trifluoromethoxy-phenylamino]-pyrimidin-4-yl}-4-oxo-1,4,6,7-tetrahydro-pyrrolo[3,2-c]pyridine-5-carboxylic acid tert-butyl ester (25 mg, 0.037 mmol) in tetrahydrofuran (1 mL), 4M HCl in dioxane (0.4 mL) were added. The solution was stirred at room temperature over night. The solvent was evaporated under vacuo to yield 22 mg (98%) of the title compound as a beige powder.

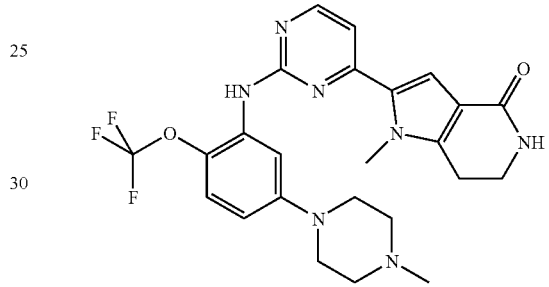

1H NMR (400 MHz, DMSO-d$_6$) δ ppm 2.83 (d, J=4.76 Hz, 3 H) 2.84-2.88 (m, 2 H) 3.03-3.21 (m, 4 H) 3.38-3.52 (m, 4 H) 3.74 (s, 3 H) 3.83 (d, J=10.85 Hz, 2 H) 6.91 (d, J=6.10 Hz, 1 H) 7.21-7.23 (m, 2 H) 7.30 (d, J=8.78 Hz, 1 H) 7.37 (d, J=2.93 Hz, 1 H) 8.30 (d, J=5.73 Hz, 1 H) 9.20 (br. s., 1 H) 10.51 (br. s., 1 H); MS (ESI): 502 [M+H]$^+$.

According to the same method, but employing the suitable starting material, the following compounds were prepared:

1-(2-hydroxy-ethyl)-2-{2-[5-(4-methyl-piperazin-1-yl)-2-trifluoromethoxy-phenylamino]-pyrimidin-4-yl}-1,5,6,7-tetrahydro-pyrrolo[3,2-c]pyridin-4-one (A5C3M2)

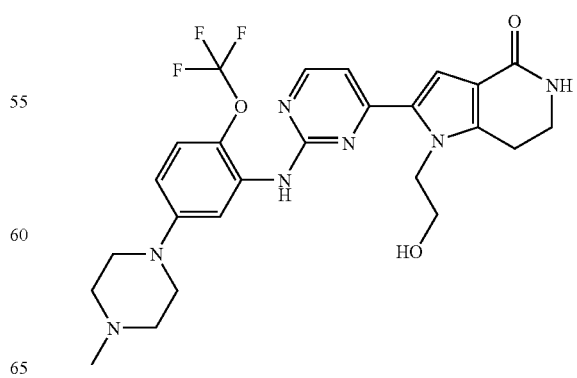

MS (ESI): 454 [M+H]$^+$.

1H NMR (400 MHz, DMSO-d$_6$) δ ppm 2.23 (s, 3 H) 2.41-2.49 (m, 4 H) 2.87 (t, J=6.89 Hz, 2 H) 3.13-3.18 (m, 4 H) 3.35-3.41 (m, 4 H) 4.35 (t, J=4.63 Hz, 2 H) 4.62 (t, J=5.49 Hz, 1 H) 6.82 (dd, J=9.14, 2.93 Hz, 1 H) 7.09 (t, J=2.26 Hz, 1 H) 7.14 (d, J=5.49 Hz, 1 H) 7.16-7.18 (m, 2 H) 7.22 (dd, J=9.14, 1.22 Hz, 1 H) 8.26 (d, J=5.49 Hz, 1 H) 8.74 (s, 1 H); MS (ESI): 454 [M+H]$^+$.

1-(2-hydroxy-ethyl)-2-{2-[2-methoxy-5-(4-methyl-piperazin-1-yl)-phenylamino]-pyrimidin-4-yl}-1,5,6,7-tetrahydro-pyrrolo[3,2-c]pyridin-4-one (A5C4M2)

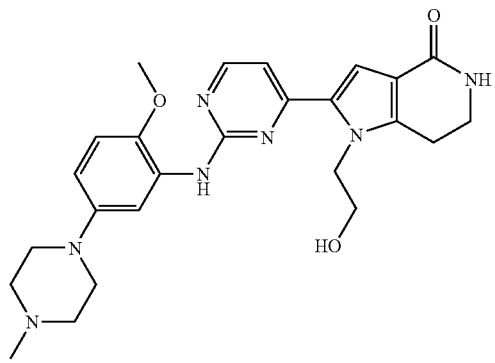 [SMILES: COc1ccc(N2CCN(C)CC2)cc1Nc1nccc(-c2cc3c(n2CCO)CCNC3=O)n1]

1H NMR (400 MHz, DMSO-d$_6$) δ ppm 2.30-2.36 (m, 3 H) 2.54-2.65 (m, 4 H) 2.89 (t, J=6.89 Hz, 2 H) 3.07 (br. s., 4 H) 3.41-3.46 (m, 4 H) 3.76 (s, 3 H) 4.42 (t, J=5.18 Hz, 2 H) 4.70 (t, J=5.43 Hz, 1 H) 6.67 (dd, J=8.78, 2.93 Hz, 1 H) 6.93 (d, J=9.02 Hz, 1 H) 7.11 (br. s., 1 H) 7.12 (d, J=5.37 Hz, 1 H) 7.15 (s, 1 H) 7.54 (d, J=2.19 Hz, 1 H) 8.08 (s, 1 H) 8.30 (d, J=5.37 Hz, 1 H); MS (ESI): 478 [M+H]$^+$ According to the same method, but employing the suitable starting material, the following compound was prepared:

1-(2-hydroxy-ethyl)-5-{2-[5-(4-methyl-piperazin-1-yl)-2-trifluoromethoxy-phenylamino]-pyrimidin-4-yl}-1H-pyrrole-3-carboxylic acid amide (A5B3C3M1)

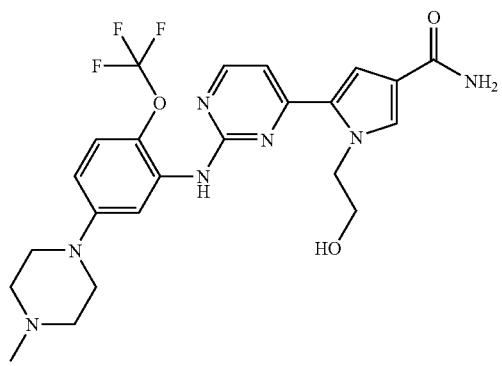 [SMILES: CN1CCN(c2ccc(OC(F)(F)F)c(Nc3nccc(-c4cc(C(N)=O)cn4CCO)n3)c2)CC1]

1H NMR (400 MHz, DMSO-d$_6$) δ ppm 2.40 (br. s., 3 H) 2.68 (br. s., 4 H) 3.21 (br. s., 4 H) 3.27-3.39 (m, 2 H) 4.35 (t, J=4.82 Hz, 2 H) 4.62 (t, J=5.36 Hz, 1 H) 6.82 (br. s., 1 H) 6.84 (dd, J=9.14, 2.93 Hz, 1 H) 7.01 (d, J=5.36 Hz, 1 H) 7.20-7.26 (m, 2 H) 7.30 (d, J=1.95 Hz, 1 H) 7.39 (br. s., 1 H) 7.46 (d, J=1.83 Hz, 1 H) 8.31 (d, J=5.36 Hz, 1 H) 8.81 (s, 1 H); MS (ESI): 506 [M+H]$^+$ Example 8

Step (a). 2-(2-iodo-pyrimidin-4-yl)-4-oxo-1-(2,2,2-trifluoro-ethyl)-1,4,6,7-tetrahydro-pyrrolo[3,2-c]pyridine-5-carboxylic acid tert-butyl ester

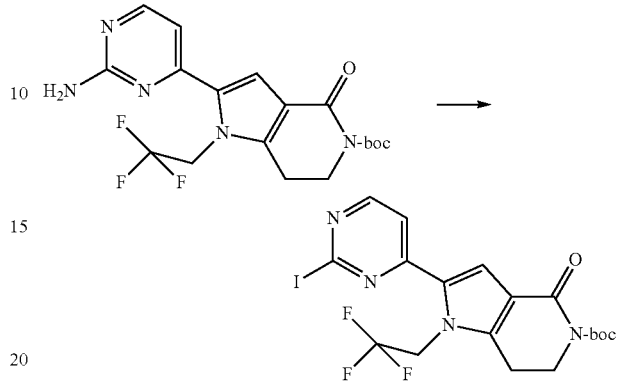

To a well stirred suspension of 2-(2-amino-pyrimidin-4-yl)-4-oxo-1-(2,2,2-trifluoro-ethyl)-1,4,6,7-tetrahydro-pyrrolo[3,2-c]pyridine-5-carboxylic acid tert-butyl ester prepared as reported in Example 9 (180 mg, 0.43 mmol) in dimethoxyethane (10 mL) under N$_2$, cesium iodide (170 mg, 0.65 mmol), bisublimated iodine (83 mg, 0.33 mmol), copper iodide (37 mg, 0.20 mmol) and isopentyl nitrite (0.13 mL, 0.98 mmol) were added in sequence. The reaction mixture was stirred vigorously at 80° C. for 4 hours. After cooling in a ice-water bath, the solid was filtered off. The filtrate was diluted with dichloromethane (100 mL), washed with 30% ammonium hydroxide (50 mL), sodium thiosulphate (50 mL), brine (50 mL), dried over anhydrous Na$_2$SO$_4$ and concentrated. Purification by flash chromatography on silica gel (eluant: dichloromethane/hexane 1/1) afforded 80 mg (35%) of the title compound as solid.

MS (ESI): 523 [M+H]$^+$.

According to the same method, but employing the suitable starting material, the following compound was prepared:

2-(2-iodo-pyrimidin-4-yl)-1-methyl-4-oxo-1,4,6,7-tetrahydro-pyrrolo[3,2-c]pyridine-5-carboxylic acid tert-butyl ester 1H NMR (400 MHz, DMSO-d$_6$) δ ppm 1.48 (s, 9 H) 2.99 (t, J=6.40 Hz, 2 H) 3.89 (s, 3 H) 3.99 (t, 2 H) 7.43 (s, 1 H) 7.91 (d, J=5.49 Hz, 1 H) 8.41 (d, J=5.49 Hz, 1 H); MS (ESI): 455 [M+H]$^+$.

Step (b). 2-{2-[5-(4-methyl-piperazin-1-yl)-2-trifluoromethoxy-phenylamino]-pyrimidin-4-yl}-4-oxo-1-(2,2,2-trifluoro-ethyl)-1,4,6,7-tetrahydro-pyrrolo[3,2-c]pyridine-5-carboxylic acid tert-butyl ester

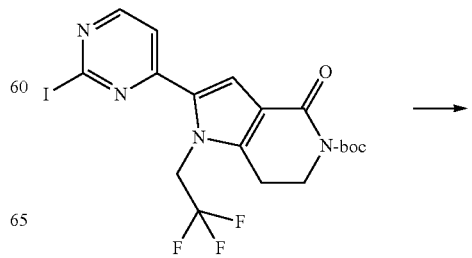

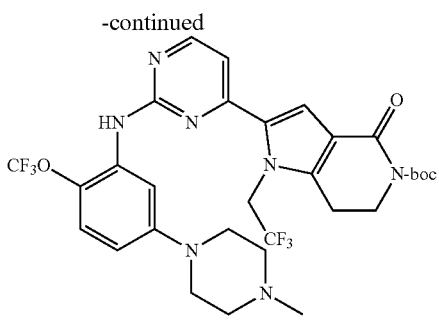

Palladium acetate [Pd(OAc)₂] (4 mg, 0.015 mmol), (±)-BINAP (9 mg, 0.015 mmol) and dimethylformamide (1 mL) were charged to a round-bottom flask flushed with argon. The flask was evacuated and backfilled with argon. The mixture was stirred under argon for 30 minutes and added to a mixture of 5-(4-methyl-piperazin-1-yl)-2-trifluoromethoxy-phenylamine (50 mg, 0.18 mmol), 2-(2-iodo-pyrimidin-4-yl)-4-oxo-1-(2,2,2-trifluoro-ethyl)-1,4,6,7-tetrahydro-pyrrolo[3,2-c]pyridine-5-carboxylic acid tert-butyl ester (80 m, 0.15 mmol), and potassium carbonate (205 g, 1.50 mmol) in dimethylformamide (3 mL). The resulting mixture was stirred at 80° C. for 2 hours under argon. After cooling to room temperature, the reaction mixture was filtered on a pad of celite. The solvent was concentrated, the crude solid was purified by flash chromatography on silica gel (eluant: dichloromethane/methanol 9/1) to afford 25 mg (25%) of the title compound as white solid.

MS (ESI): 670 [M+H]⁺.

According to the same method, but employing the suitable starting material, the following compound was prepared:

1-methyl-2-{2-[5-(4-methyl-piperazin-1-yl)-2-trifluoromethoxy-phenylamino]-pyrimidin-4-yl}-4-oxo-1,4,6,7-tetrahydro-pyrrolo[3,2-c]pyridine-5-carboxylic acid tert-butyl ester

MS (ESI): 602 [M+H]⁺.

Step (d). 2-{2-[5-(4-methyl-piperazin-1-yl)-2-trifluoromethoxy-phenylamino]-pyrimidin-4-yl}-1-(2,2,2-trifluoro-ethyl)-1,5,6,7-tetrahydro-pyrrolo[3,2-c]pyridin-4-one hydrochloride (A3C3M2)

To a solution of 2-{2-[5-(4-methyl-piperazin-1-yl)-2-trifluoromethoxy-phenylamino]-pyrimidin-4-yl}-4-oxo-1-(2,2,2-trifluoro-ethyl)-1,4,6,7-tetrahydro-pyrrolo[3,2-c]pyridine-5-carboxylic acid tert-butyl ester (25 mg, 0.037 mmol) in tetrahydrofuran (1 mL), 4M HCl in dioxane (0.4 mL) were added. The solution was stirred at room temperature overnight. The solvent was evaporated under vacuo to yield 22 mg (98%) of the title compound as a beige powder.

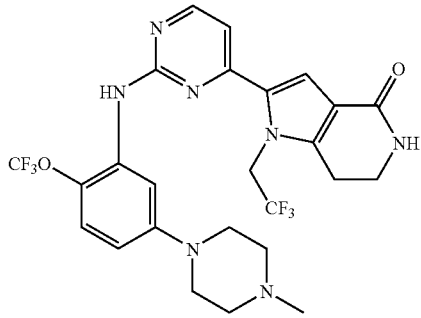

1H NMR (400 MHz, DMSO-d₆) δ ppm 2.80-2.86 (m, 3 H) 2.89-2.96 (m, 2 H) 3.03-3.23 (m, 4 H) 3.32-3.46 (m, 2 H) 3.46-3.55 (m, 2 H) 3.79-3.89 (m, 2 H) 5.61-5.73 (m, 2 H) 6.91 (dd, J=9.08, 2.74 Hz, 1 H) 7.22 (d, J=5.37 Hz, 1 H) 7.27 (s, 1 H) 7.28-7.32 (m, 2 H) 8.33 (d, J=5.37 Hz, 1 H) 9.19 (s, 1 H) 10.35 (br. s., 1 H); MS (ESI): 570 [M+H]⁺.

According to the same method, but employing the suitable starting material, the following compound was prepared:

1-methyl-2-{2-[5-(4-methyl-piperazin-1-yl)-2-trifluoromethoxy-phenylamino]-pyrimidin-4-yl}-1,5,6,7-tetrahydro-pyrrolo[3,2-c]pyridin-4-one hydrochloride (A1C3M2)

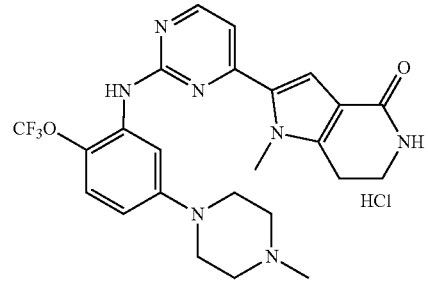

1H NMR (400 MHz, DMSO-d₆) δ ppm 2.83 (d, J=4.76 Hz, 3 H) 2.84-2.88 (m, 2 H) 3.03-3.21 (m, 4 H) 3.38-3.52 (m, 4 H) 3.74 (s, 3 H) 3.83 (d, J=10.85 Hz, 2 H) 6.91 (d, J=6.10 Hz, 1 H) 7.21-7.23 (m, 2 H) 7.30 (d, J=8.78 Hz, 1 H) 7.37 (d, J=2.93 Hz, 1 H) 8.30 (d, J=5.73 Hz, 1 H) 9.20 (br. s., 1 H) 10.51 (br. s., 1 H); MS (ESI): 502 [M+H]⁺.

Example 9

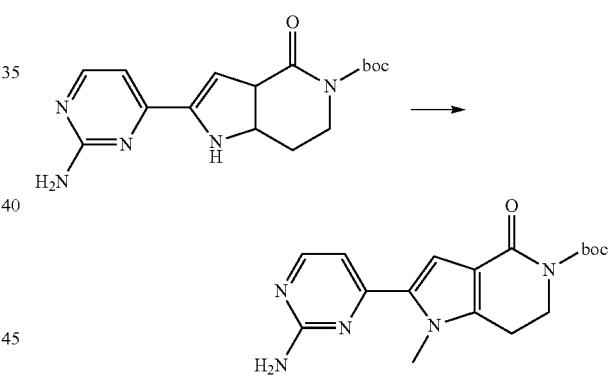

To a solution of 2-(2-Amino-pyrimidin-4-yl)-4-oxo-1,4,6,7-tetrahydro-pyrrolo[3,2-c]pyridine-5-carboxylic acid tert-butyl ester prepared as described in WO02007/068728 (1 g, 3.04 mmol) in anhydrous DMF (15 mL), Cs₂CO₃ (1.5 g, 4.56 mml) and iodomethane (0.23 ml, 3.65 mmol) were added and the mixture was stirred for 3 hours at room temperature. The solvent was concentrated, the crude solid was purified by flash chromatography on silica gel (eluant: ethylacetate/hexane 8/2) to afford 1.04 g (90%) as a solid.

2-(2-amino-pyrimidin-4-yl)-1-methyl-4-oxo-1,4,6,7-tetrahydro-pyrrolo[3,2-c]pyridine-5-carboxylic acid tert-butyl ester ¹H NMR (400 MHz, DMSO-d₆) δ ppm 1.49 (s, 9 H) 2.94-2.99 (m, 2 H) 3.95 (s, 3 H) 3.96-4.01 (m, 2 H) 6.58 (b.s., 2 H) 6.91 (d, J=5.24 Hz, 1 H) 7.10 (s, 1 H) 8.17 (d, J=5.24 Hz, 1 H); MS (ESI): 344 [M+H]⁺.

According to the same method, but employing the suitable starting material, the following compound was prepared

2-(2-amino-pyrimidin-4-yl)-1-(2-fluoro-ethyl)-4-oxo-1,4,6,7-tetrahydro-pyrrolo[3,2-c]pyridine-5-carboxylic acid tert-butyl ester $^1$H NMR (400 MHz, DMSO-$d_6$) δ ppm 1.48 (s, 9 H) 2.93-3.01 (m, 2 H) 3.93-4.01 (m, 2 H) 4.66-4.91 (m, 4 H) 6.59 (s, 2 H) 6.97 (d, J=5.24 Hz, 1 H) 7.23 (s, 1 H) 8.16 (d, J=5.24 Hz, 1 H); MS (ESI): 376 [M+H]$^+$.

2-(2-amino-pyrimidin-4-yl)-4-oxo-1-(2,2,2-trifluoro-ethyl)-1,4,6,7-tetrahydro-pyrrolo[3,2-c]pyridine-5-carboxylic acid tert-butyl ester $^1$H NMR (400 MHz, DMSO-$d_6$) δ ppm 1.49 (s, 9 H) 3.03 (t, J=6.34 Hz, 2 H) 4.00 (t, J=6.34 Hz, 2 H) 5.80-5.97 (m, 2 H) 6.71 (s, 2 H) 6.97 (d, J=5.24 Hz, 1 H) 7.24 (s, 1 H) 8.19 (d, J=5.24 Hz, 1 H); MS (ESI): 412 [M+H]$^+$.

2-(2-amino-pyrimidin-4-yl)-1-(2-hydroxy-ethyl)-4-oxo-1,4,6,7-tetrahydro-pyrrolo[3,2-c]pyridine-5-carboxylic acid tert-butyl ester $^1$H NMR (400 MHz, DMSO-$d_6$) δ ppm 1.49 (s, 9 H) 2.95-3.00 (m, 2 H) 3.55-3.60 (m, 2 H) 3.72 (t, J=5.80 Hz, 2 H) 4.68 (t, J=5.80 Hz, 2 H) 4.75 (b.s., 1 H) 6.80 (b.s., 2 H) 7.02 (d, J=5.24 Hz, 1 H) 7.16 (s, 1 H) 8.17 (d, J=5.24 Hz, 1 H); MS (ESI): 374 [M+H]$^+$.

---

---

The invention claimed is:

1. A compound of formula (I):

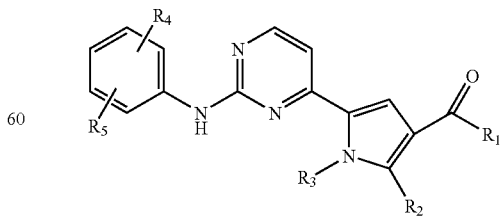

wherein:
  $R_1$ is —OR' or —NR'R", wherein R' and R" are, each independently, hydrogen or an optionally substituted group selected from straight or branched $C_1$-$C_6$ alkyl, $C_2$-$C_6$ alkenyl, $C_2$-$C_6$ alkynyl, $C_3$-$C_6$ cycloalkyl and heterocyclyl;

$R_2$ is hydrogen, or $R_1$ and $R_2$ taken together are a —NH—CH$_2$—CH$_2$— chain and form a 6-membered lactam fused with the pyrrole ring;

$R_3$ is an optionally substituted straight or branched $C_1$-$C_6$ alkyl;

$R_4$ and $R_5$ are, each independently, halogen, a group —O—$R_3$, or an optionally substituted group selected from polyfluorinated alkoxy, and heterocyclyl, wherein $R_3$ is as defined above;

and pharmaceutically acceptable salts thereof.

2. A compound of formula (I) as defined in claim 1 wherein:

$R_1$ is —OH or —NR'R", wherein R' and R" are as defined in claim 1.

3. A compound of formula (I) as defined in claim 1 or 2 wherein the position of the substituents $R_4$ and $R_5$ are as reported below:

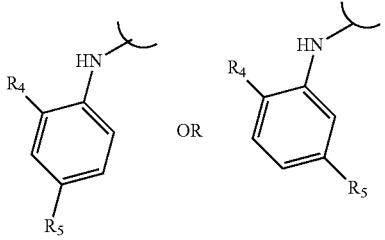

wherein $R_4$ and $R_5$ are, each independently, halogen, a group —O—$R_3$, or an optionally substituted group selected from polyfluorinated alkoxy, and heterocyclyl, wherein $R_3$ is as defined in claim 1.

4. A compound of formula (I) as defined in claim 1, wherein:

$R_1$ and $R_2$ taken together are a —NH—CH$_2$—CH$_2$— chain and form a 6-membered lactam fused with the pyrrole ring, and $R_3$, $R_4$ and $R_5$ are as defined in claim 1.

5. A compound or a pharmaceutically acceptable salt thereof which is selected from the group consisting of:

5-[2-(5-bromo-2-trifluoromethoxy-phenylamino)-pyrimidin-4-yl]-1-methyl-1H-pyrrole-3-carboxylic acid ethyl ester (A1B1C1M1);

5-[2-(5-bromo-2-methyl-phenylamino)-pyrimidin-4-yl]-1-methyl-1H-pyrrole-3-carboxylic acid (A1B2C1M1);

5-[2-(5-bromo-2-trifluoromethoxy-phenylamino)-pyrimidin-4-yl]-1-methyl-1H-pyrrole-3-carboxylic acid amide (A1B3C1M1);

1-methyl-5-[2-(5-piperazin-1-yl-2-trifluoromethoxy-phenylamino)-pyrimidin-4-yl]-1H-pyrrole-3-carboxylic acid amide (A1B3C2M1);

1-methyl-5-{2-[5-(4-methyl-piperazin-1-yl)-2-trifluoromethoxy-phenylamino]-pyrimidin-4-yl}-1H-pyrrole-3-carboxylic acid ethyl ester (A1B1C3M1);

1-methyl-5-{2-[5-(4-methyl-piperazin-1-yl)-2-trifluoromethoxy-phenylamino]-pyrimidin-4-yl}-1H-pyrrole-3-carboxylic acid (A1B2C3M1);

1-methyl-5-{2-[5-(4-methyl-piperazin-1-yl)-2-trifluoromethoxy-phenylamino]-primidin-4-yl}-1H-pyrrole-3-carboxylic acid amide (A1B3C3M1);

5-[2-(5-bromo-2-trifluoromethoxy-phenylamino)-primidin-4-yl]-1-(2-fluoro-ethyl)-1H-pyrrole-3-carboxylic acid ethyl ester (A2B1C1M1);

5-[2-(5-bromo-2-trifluoromethoxy-phenylamino)-pyrimidin-4-yl]-1-(2,2,2-trifluoro-ethyl)-1H-pyrrole-3-carboxylic acid ethyl ester (A3B1C1M1);

5-[2-(5-bromo-2-trifluoromethoxy-phenylamino)-pyrimidin-4-yl]-1-(2-fluoro-ethyl)-1H-pyrrole-3-carboxylic acid amide (A2B3C1M1);

5-{2-[5-(4-methyl-piperazin-1-yl)-2-trifluoromethoxy-phenylamino]-pyrimidin-4-yl}-1-(2,2,2-trifluoro-ethyl)-1H-pyrrole-3-carboxylic acid ethyl ester (A3B1C3M1);

5-{2-[5-(4-methyl-piperazin-1-yl)-2-trifluoromethoxy-phenylamino]-pyrimidin-4-yl}-1-(2,2,2-trifluoro-ethyl)-1H-pyrrole-3-carboxylic acid (A3B2C3M1);

5-[2-(5-bromo-2-trifluoromethoxy-phenylamino)-pyrimidin-4-yl]-1-(2,2,2-trifluoro-ethyl)-1H-pyyrole-3-carboxylic acid amide (A3B3C1M);

5-{2-[5-(4-methyl-piperazin-1-yl)-2-trifluoromethoxy-phenylamino]-pyrimidin-4-yl}-1-(2,2,2-trifluoro-ethyl)-1H-pyrrole-3-carboxylic acid amide (A3B3C3M1);

1-methyl-2-{2-[5-(4-methyl-piperazin-1-yl)-2-trifluoromethoxy-phenylamino]-pyrimidin-4-yl}-1,5,6,7-tetrahydro-pyrrolo[3,2-c]pyridin-4-one (A1C3M2), 2-{2-[5-(4-methyl-piperazin-1-yl)-2-trifluoromethoxy-phenylamino]-pyrimidin-4-yl}-1-(2,2,2-trifluoro-ethyl)-1,5,6,7-tetrahydro-pyrrolo[3,2-c]pyridin-4-one (A3C3M2), and 1-(2-hydroxy-ethyl)-2-{2-[5-(4-methyl-piperazin-1-yl)-2-trifluoromethoxy-phenylamino]-pyrimidin-4-yl}-1,5,6,7-tetrahydro-pyrrolo[3,2-c]pyridin-4-one (A5C3M2).

6. A process for preparing a compound of formula (I) as defined in claim 1, characterized in that the process comprises:

d) deprotecting a compound of formula (XIII):

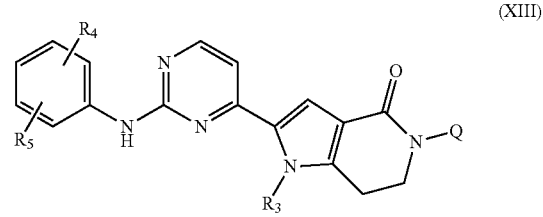

wherein $R_3$, $R_4$ and $R_5$ are as defined in claim 1 and Q is a suitable protecting amino group, the suitable protecting amino group comprising t-butoxycarbonyl, to give a compound of formula (Ia):

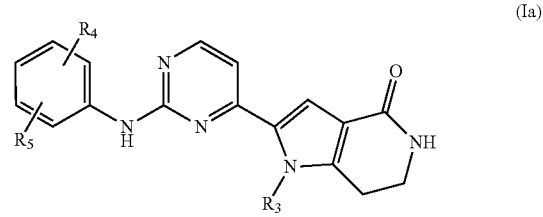

wherein $R_3$, $R_4$ and $R_5$ are as defined in claim 1; or d') reacting a compound of formula (VIII):

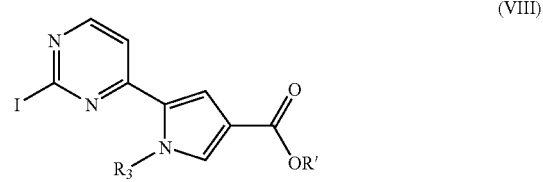

wherein R' is as defined in claim 1 except hydrogen and R₃ is as defined in claim 1, with an optionally substituted arylamine of formula (IX):

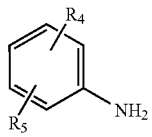

(IX)

wherein R₄ and R₅ are as defined in claim 1, under reductive conditions, to give a compound of formula (Ib):

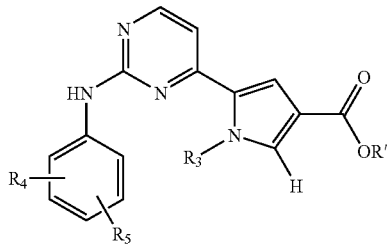

(Ib)

wherein R' is as defined in claim 1 except hydrogen and R₃, R₄ and R₅ are as defined in claim 1; or d") reacting a compound of formula (VII):

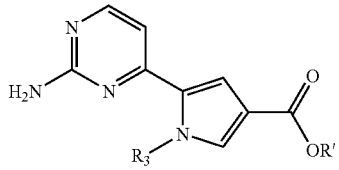

(VII)

wherein R' is as defined in claim 1 except hydrogen and R₃ is as defined in claim 1, with an optionally substituted iodophenyl derivative of formula (XVII):

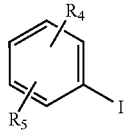

(XVII)

wherein R₄ and R₅ are as defined in claim 1, under reductive conditions, to give a compound of formula (Ib) as defined above;

optionally separating the resulting compound into the single isomers, converting the compound into a different compound of formula (I) and/or into a pharmaceutically acceptable salt if desired.

7. A process according to claim 6, characterized in that the compound of formula (XIII) as defined in claim 6, is prepared according to the following steps:

a) reacting a compound of formula (XIV):

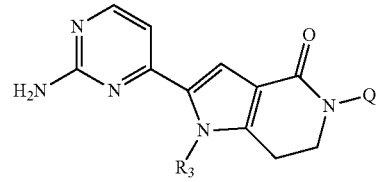

(XIV)

wherein R₃ is as defined in claim 1, with isoamyl nitrite in presence of a iodide source, the iodide source comprising at least one of copper iodide, cesium iodide and iodine, to give a compound of formula (XV):

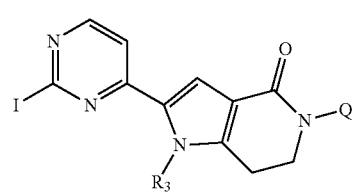

(XV)

wherein R₃ is as defined in claim 1 and Q is as defined in claim 6;

b) reacting the resulting compound of formula (XV) with an optionally substituted arylamine of formula (IX) as defined in claim 6, under reductive conditions, to give a compound of formula (XIII) as defined in claim 6; or c) reacting a compound of formula (XIV) as defined above, with an optionally substituted iodophenyl derivative of formula (XVII) as defined in claim 6, under reductive conditions, to give a compound of formula (XIII) as defined in claim 6.

8. A process according to claim 6, characterized in that the compound of formula (VII) and (VIII) as defined in claim 6, are prepared according to the following steps:

e) reacting the compound of formula (II):

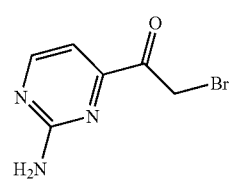

(II)

with a compound of formula (X):

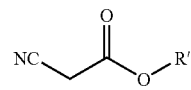

(X)

wherein R' is as above defined except hydrogen, in presence of sodium metal, to give a compound of formula (III):

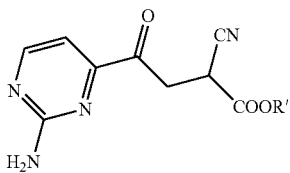

(III)

wherein R' is as above defined except hydrogen;
f) reacting the resulting compound of formula (III) hydrochloric or hydrobromic acid, to give a compound of formula (IV):

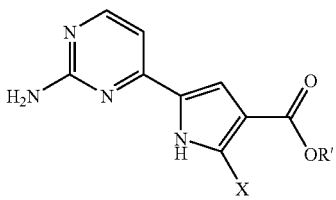

(IV)

wherein R' is as above defined except hydrogen and X is chlorine or bromine;
g) reducing the resulting compound of formula (IV), to give a compound of formula (V):

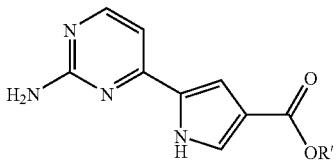

(V)

wherein R' is as above defined except hydrogen;
h) reacting the resulting compound of formula (V) with a compound of formula (VI):

$R_3$—Y  (VI)

wherein $R_3$ is as defined in claim 1 and Y is halogen or a suitable leaving group, the halogen or suitable leaving group comprising one of toluensulfonyl and trifluoromethanesulfonyl in the presence of a base, to give a compound of formula (VII) as defined in claim 6;
i) reacting the resulting compound of formula (VII) with isoamyl nitrite in presence of a iodide source such as copper (I) iodide, cesium iodide, iodine or a mixture of them, to give a compound of formula (VIII) as defined in claim 6.

9. A process according to claim 6, characterized in that the optional conversion of a compound of formula (I) into an other compound of formula (I), is carried out in one of the following ways:

I) converting a compound of formula (Ib) as defined in claim 6, into a compound of formula (I) wherein $R_1$ is a group —OH or corresponding salt through acidic or basic hydrolysis;

II) converting a compound of formula (Ib) as defined above, into a compound of formula (I) wherein $R_1$ is a group —NR'R" by treatment with an amine of formula R'R"—NH (XII), as defined above, in a sealed tube;

III) converting a compound of formula (I) wherein $R_1$ is —OH or corresponding salt into a compounds of formula (I) wherein $R_1$ is a group —NR'R", through reaction with an amine of formula R'R"—NH (XII), wherein R' and R" are as defined in claim 1, under basic conditions and in the presence of a suitable condensing agent;

IV) converting a compound of formula (I) wherein $R_1$ is —NR'R" and $R_5$ is bromine, into a compound of formula (I) wherein $R_1$ is as defined above and $R_5$ is heterocyclyl, wherein $R_3$ is as defined above, under reductive conditions, by treatment with an amine of formula R'''R'''—NH (XI) wherein R''' and R'''' are, each independently, hydrogen or an optionally substituted group selected from straight or branched $C_1$-$C_6$ alkyl, $C_2$-$C_6$ alkenyl, $C_2$-$C_6$ alkynyl, $C_3$-$C_6$ cycloalkyl and heterocyclyl, or R''' and R'''' taken together with the nitrogen atom to which they are bonded, may form an optionally substituted heterocyclyl group, V) converting a compound of formula (Ia) wherein $R_5$ is bromine, into a compound of formula (Ia) wherein $R_5$ is heterocyclyl, wherein $R_3$ is as defined above, by treatment with an amine of formula R'''R''''—NH (XI) as defined above, under reductive conditions.

10. A method for treating a disease selected from the group consisting of colon cancer prostate cancer, breast cancer, ovarian cancer, melanoma, leukemia, lymphoma, and combinations thereof, which comprises administering to a mammal in need thereof an effective amount of a compound of formula (I) as defined in claim 1.

11. The method according to claim 10 further comprising subjecting the mammal in need thereof to a radiation therapy or chemotherapy regimen in combination with at least one cytostatic or cytotoxic agent.

12. The method according to claim 10 wherein the mammal in need thereof is a human.

13. A method for inhibiting PLK-1 and PLK-3 activity which comprises contacting the said protein with an effective amount of a compound as defined in claim 1.

14. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

15. A product or kit comprising a compound of formula (I) or a pharmaceutically acceptable salt thereof, as defined in claim 1, or pharmaceutical compositions thereof as defined in claim 14 and one or more chemotherapeutic agents, as a combined preparation for simultaneous, separate or sequential use in anticancer therapy.

* * * * *

SEQUENCE LISTING

```
<160> NUMBER OF SEQ ID NOS: 3

<210> SEQ ID NO 1
<211> LENGTH: 82
<212> TYPE: DNA
<213> ORGANISM: Artificial Sequence
<220> FEATURE:
<223> OTHER INFORMATION: forward primer

<400> SEQUENCE: 1
ggggacaagt ttgtacaaaa aagcaggctt attcgaaaac ctgtattttc agggccctag    60
tgctgcagtg actgcaggga ag                                             82

<210> SEQ ID NO 2
<211> LENGTH: 60
<212> TYPE: DNA
<213> ORGANISM: Artificial Sequence
<220> FEATURE:
<223> OTHER INFORMATION: reverse primer

<400> SEQUENCE: 2
ggggaccact ttgtacaaga aagctgggtt tcactattta ttgaggactg tgaggggctt    60

<210> SEQ ID NO 3
<211> LENGTH: 7
<212> TYPE: PRT
<213> ORGANISM: Artificial Sequence
<220> FEATURE:
<223> OTHER INFORMATION: kinase assay

<400> SEQUENCE: 3

Leu Arg Arg Trp Ser Leu Gly
1               5
```